US011471660B2

(12) United States Patent
Malkowski et al.

(10) Patent No.: US 11,471,660 B2
(45) Date of Patent: Oct. 18, 2022

(54) VACUUM DRIVEN SUCTION AND IRRIGATION SYSTEM

(71) Applicant: Covidien LP, Mansfield, MA (US)

(72) Inventors: Jaroslaw Malkowski, Trumbull, CT (US); Kenneth Horton, South Glastonbury, CT (US); Lau Ow, Shatin (HK)

(73) Assignee: Covidien LP, Mansfield, MA (US)

( * ) Notice: Subject to any disclaimer, the term of this patent is extended or adjusted under 35 U.S.C. 154(b) by 444 days.

(21) Appl. No.: 16/656,973

(22) Filed: Oct. 18, 2019

(65) Prior Publication Data

US 2020/0129751 A1 Apr. 30, 2020

Related U.S. Application Data

(63) Continuation-in-part of application No. 16/589,651, filed on Oct. 1, 2019.

(60) Provisional application No. 62/750,301, filed on Oct. 25, 2018.

(51) Int. Cl.
*A61M 39/22* (2006.01)
*A61M 3/02* (2006.01)
*A61M 1/00* (2006.01)

(52) U.S. Cl.
CPC .......... *A61M 39/227* (2013.01); *A61M 1/743* (2021.05); *A61M 1/774* (2021.05); *A61M 3/0254* (2013.01); *A61B 2217/005* (2013.01); *A61B 2217/007* (2013.01)

(58) Field of Classification Search
CPC .............. A61M 1/0041; A61M 1/0058; A61M 1/0072; A61M 3/0254; A61M 3/0233; A61M 3/0237; A61M 5/148; F04B 43/0736; F04B 43/0054; F04B 43/06; F04B 9/135; F04B 9/1207; A61J 1/10
See application file for complete search history.

(56) References Cited

U.S. PATENT DOCUMENTS

| | | | | |
|---|---|---|---|---|
| 2,915,222 A | * | 12/1959 | Purinton | A01G 25/145 222/215 |
| 3,572,980 A | * | 3/1971 | Hollyday | F04B 45/043 417/413.1 |
| 3,640,277 A | * | 2/1972 | Adelberg | A61M 5/1483 222/61 |
| 3,960,294 A | * | 6/1976 | Bernard | B05C 17/0052 222/103 |

(Continued)

OTHER PUBLICATIONS

European Search Report dated Jun. 24, 2020, issued in EP Appln. No. 19205465, 13 pages.

(Continued)

*Primary Examiner* — Scott J Medway

(57) ABSTRACT

A vacuum assisted suction and irrigation system includes a suction and irrigation wand, an irrigation fluid supply, a vacuum source, and a fluid pump. The vacuum source is connected to a suction valve of the suction and irrigation wand to provide suction within the suction and irrigation wand. The irrigation fluid supply is connected to the suction and irrigation wand via the fluid pump to supply pressurized irrigation fluid to the suction and irrigation wand. The vacuum source is connected to the fluid pump to pressurize the irrigation fluid being delivered to the suction and irrigation wand.

21 Claims, 19 Drawing Sheets

(56) References Cited

U.S. PATENT DOCUMENTS

| | | | |
|---|---|---|---|
| 4,033,479 A * | 7/1977 | Fletcher | G01F 11/08 222/61 |
| 4,284,209 A * | 8/1981 | Barbour, Jr. | A61M 1/029 222/103 |
| 4,381,180 A * | 4/1983 | Sell | F04B 43/0736 417/393 |
| 4,386,888 A * | 6/1983 | Verley | F01L 25/063 417/393 |
| 4,604,089 A * | 8/1986 | Santangelo | A61M 3/0212 604/35 |
| 4,613,327 A * | 9/1986 | Tegrarian | A61M 5/172 604/141 |
| 4,735,613 A * | 4/1988 | Bellin | A61M 5/1483 D24/111 |
| 4,981,418 A * | 1/1991 | Kingsford | F04B 43/009 417/63 |
| 5,125,910 A * | 6/1992 | Freitas | A61M 1/774 604/249 |
| 5,188,591 A * | 2/1993 | Dorsey, III | A61M 1/774 604/35 |
| 5,391,060 A * | 2/1995 | Kozumplik, Jr. | F04B 43/0736 417/393 |
| 5,391,145 A * | 2/1995 | Dorsey, III | A61M 1/774 604/35 |
| 5,399,166 A * | 3/1995 | Laing | A61M 5/1483 604/141 |
| 5,415,531 A * | 5/1995 | Cavanaugh | F04B 9/133 417/403 |
| 5,472,420 A * | 12/1995 | Campbell | A61M 5/148 604/67 |
| 5,536,254 A * | 7/1996 | McVay | A61M 3/022 604/135 |
| 5,542,918 A | 8/1996 | Atkinson | |
| 5,573,504 A * | 11/1996 | Dorsey, III | A61M 1/774 604/35 |
| 5,720,728 A * | 2/1998 | Ford | A61M 5/1483 604/141 |
| 5,758,563 A * | 6/1998 | Robinson | F01L 31/02 417/393 |
| 5,807,313 A * | 9/1998 | Delk | A61M 3/0258 604/35 |
| 5,857,592 A * | 1/1999 | Hyldgaard | B65D 75/5866 222/105 |
| 5,927,954 A * | 7/1999 | Kennedy | F04B 43/0736 417/397 |
| 6,079,959 A * | 6/2000 | Kingsford | F04B 53/164 417/393 |
| 6,142,749 A * | 11/2000 | Jack | F04B 53/1002 92/99 |
| 6,176,847 B1 * | 1/2001 | Humphreys, Jr. | A61M 3/0208 604/246 |
| 6,419,654 B1 * | 7/2002 | Kadan | A61M 1/774 600/101 |
| 6,436,072 B1 * | 8/2002 | Kullas | A61M 1/0058 417/477.2 |
| 6,824,528 B1 * | 11/2004 | Faries, Jr. | A61M 5/44 604/113 |
| 6,958,058 B1 | 10/2005 | Hunter, Sr. et al. | |
| 7,399,168 B1 * | 7/2008 | Eberwein | F04B 43/0736 92/48 |
| 7,458,309 B2 * | 12/2008 | Simmons | F04B 43/0736 417/393 |
| 7,867,196 B1 * | 1/2011 | Coplin | A61M 3/0258 604/131 |
| 8,162,923 B2 * | 4/2012 | Adams | A61M 5/14248 604/890.1 |
| 8,262,366 B2 * | 9/2012 | Simmons | F04B 45/043 417/393 |
| 8,534,282 B2 * | 9/2013 | Bergman | A61M 16/0078 128/205.16 |
| 9,822,770 B2 * | 11/2017 | Pabst | F04B 7/02 |
| 10,105,491 B2 * | 10/2018 | Gelblum | A61M 5/2425 |
| 11,098,707 B2 * | 8/2021 | van Boeyen | F04B 43/10 |
| 2001/0048882 A1 * | 12/2001 | Layman | F04B 43/0736 417/536 |
| 2004/0204679 A1 * | 10/2004 | Visconti | A61M 1/7413 604/131 |
| 2005/0084395 A1 | 4/2005 | Kang | |
| 2007/0092385 A1 * | 4/2007 | Petrie Pe | F04B 53/22 417/395 |
| 2007/0233003 A1 * | 10/2007 | Radgowski | A61M 1/0058 604/151 |
| 2009/0324431 A1 | 12/2009 | van Boeyen et al. | |
| 2011/0071465 A1 * | 3/2011 | Wang | A61M 1/288 604/67 |
| 2011/0224600 A1 * | 9/2011 | Orlandi | A61M 3/022 604/30 |
| 2011/0306941 A1 * | 12/2011 | Chandrasekar | A61M 3/0254 604/262 |
| 2012/0289894 A1 * | 11/2012 | Douglas | A61M 1/85 604/35 |
| 2014/0100518 A1 * | 4/2014 | Baxter | A61M 3/0216 604/93.01 |
| 2015/0297405 A1 * | 10/2015 | Bourne | A61M 1/0058 604/31 |
| 2019/0093651 A1 * | 3/2019 | Hines | F04B 17/044 |
| 2019/0301443 A1 * | 10/2019 | Willoughby | F04B 45/043 |
| 2020/0324040 A1 * | 10/2020 | Hejmowski | A61M 1/0062 |
| 2021/0123429 A1 * | 4/2021 | Teshima | F04B 53/14 |

OTHER PUBLICATIONS

European Search Report dated Mar. 24, 2020, issued in EP Appln. No. 19205465, 15 pages.

* cited by examiner

VACUUM DRIVEN SUCTION AND IRRIGATION SYSTEM

CROSS-REFERENCE TO RELATED APPLICATIONS

This application is a continuation-in-part of U.S. patent application Ser. No. 16/589,651, filed Oct. 1, 2019, which claims the benefit of U.S. Provisional Application Ser. No. 62/750,301, filed Oct. 25, 2019, the entire disclosures each of which are incorporated by reference herein.

BACKGROUND

1. Technical Description

The disclosure is directed to a suction and irrigation system and, more particularly, to a vacuum assisted suction and irrigation system.

2. Background of Related Art

Suction and irrigation systems that include a surgical instrument to provide both suction and irrigation to a surgical site are well known. Typically, such systems include a source of vacuum that is coupled to the surgical instrument to provide suction and an electric, e.g., battery powered pump to deliver irrigation fluid to the surgical instrument. Thus, two types of power sources are required to use the surgical instrument.

A continuing need exists in the surgical arts for a suction and irrigation system that can operate using a single energy source, i.e., vacuum, that is already available in an operating room.

SUMMARY

One aspect of the disclosure is directed to a vacuum assisted suction and irrigation system that includes a suction and irrigation wand, an irrigation fluid supply, a vacuum source, and a fluid pump. The suction and irrigation wand includes a proximal body portion supporting a suction valve and an irrigation valve and a distal body portion defining a fluid channel. The irrigation fluid supply is connected to the irrigation valve of the suction and irrigation wand. The irrigation valve is actuable to deliver irrigation fluid to the fluid channel of the suction and irrigation wand. The vacuum source is connected to the suction valve of the suction and irrigation wand. The suction valve is actuable to draw a vacuum within the fluid channel. The fluid pump is positioned to deliver fluid to the suction and irrigation wand. The vacuum source is connected to the fluid pump to pressurize the irrigation fluid.

In another aspect of the disclosure, a fluid pump includes a body, a first diaphragm, a second diaphragm, a first piston, a second piston, an atmosphere valve assembly, a vacuum valve assembly, and first and second frame members. The body defines a first pump chamber, a second pump chamber, a vacuum chamber, and an atmosphere channel. The vacuum chamber communicates with the vacuum source and the atmosphere channel communicates with atmosphere. The first diaphragm divides the first pump chamber into a first vacuum cavity and a first fluid cavity and the second diaphragm divides the second pump chamber into a second vacuum cavity and a second fluid cavity. The first piston is supported by the first diaphragm and the second piston is supported by the second diaphragm. The first piston is coupled to the second piston by a piston shaft such that the first and second pistons are movable in unison between first and second end stroke positions. The body defines a first bore that communicates the first vacuum cavity with the atmosphere channel, a second bore that communicates the second vacuum cavity with the atmosphere channel, a third bore that communicates the first vacuum cavity with the vacuum chamber, and a fourth bore that communicates the second vacuum cavity with the vacuum chamber. The atmosphere valve assembly includes a first valve member and a second valve member. The atmosphere valve assembly is movable between a first end stroke position in which the first valve member seals the first bore and the second bore is unsealed, and a second end stroke position in which the second seal member seals the second bore and the first bore is unsealed. The first valve member is coupled to the second valve member by a first valve shaft. The vacuum valve assembly includes a third valve member and a fourth valve member. The vacuum valve assembly is movable between a first end stroke position in which the third valve member seals the third bore and the fourth bore is unsealed, and a second end stroke position in which the fourth seal member seals the fourth bore and the third bore is unsealed. The third valve member is coupled to the fourth valve member by a second valve shaft. The first frame member interconnects first ends of the first and second valve shafts and the second frame member interconnects second ends of the first and second valve shafts.

In some aspects of the disclosure, the fluid pump is a diaphragm type pump.

In some aspects of the disclosure, the fluid pump includes a first pump chamber and a second pump chamber. The first pump chamber is divided into a first vacuum cavity and a first fluid cavity by a first diaphragm and the second pump chamber is divided into a second vacuum cavity and a second fluid cavity by a second diaphragm.

In certain aspects of the disclosure, the first diaphragm supports a first piston or shaft holder and the second diaphragm supports a second piston or shaft holder.

In aspects of the disclosure, the first piston is coupled to the second piston by a piston shaft.

In some aspects of the disclosure, the fluid pump includes a vacuum chamber and an atmosphere channel, wherein the vacuum chamber communicates with the vacuum source and the atmosphere channel communicates with atmosphere.

In certain aspects of the disclosure, the fluid pump includes a atmosphere valve assembly, a first bore communicating the first vacuum cavity with the atmosphere channel, and a second bore communicating the second vacuum cavity with the atmosphere channel.

In aspects of the disclosure, the atmosphere valve assembly includes a first valve member and a second valve member and is movable between a first position in which the first valve member seals the first bore and the second bore is unsealed, and a second position in which the second seal member seals the second bore and the first bore is unsealed.

In some aspects of the disclosure, the fluid pump includes a vacuum valve assembly, a third bore communicating the first vacuum cavity with the vacuum chamber, and a fourth bore communicating the second vacuum cavity with the vacuum chamber.

In certain aspects of the disclosure, the vacuum valve assembly includes a third valve member and a fourth valve member and is movable between a first position in which the third valve member seals the third bore and the fourth bore is unsealed, and a second position in which the fourth seal member seals the fourth bore and the third bore is unsealed.

In aspects of the disclosure, the first valve member is coupled to the second valve member by a first valve shaft and the third valve member is coupled to the fourth valve member by a second valve shaft.

In some aspects of the disclosure, the irrigation fluid supply includes a compressible pouch.

In certain aspects of the disclosure, the fluid pump includes a base member and a compression member having a first end pivotally coupled to the base member.

In aspects of the disclosure, the compressible pouch is positioned between the base member and the compression member.

In some aspects of the disclosure, the fluid pump includes a bellows that is attached to the base member and the compression member. The bellows is movable between a contracted position and an expanded position to control the pressure of irrigation fluid within the compressible pouch.

In certain aspects of the disclosure, the fluid pump includes a first frame member and a second frame member, wherein the first frame member interconnects first ends of the first and second valve shafts and the second frame member interconnects second ends of the first and second valve shafts.

In aspects of the disclosure, an inner magnet is supported on the body adjacent each of the first and second vacuum cavities of the first and second pump chambers, wherein each of the inner magnets is positioned to attract a respective one of the first and second frame members to urge the atmosphere valve assembly and the vacuum valve assembly towards one of their end stroke positions.

In aspects of the disclosure, each of the first and second pistons supports a biasing mechanism, wherein the biasing mechanism is positioned to engage a respective one of the first and second frame members to urge the first and second valve shafts to one of their end stroke positions and delay transitioning of the atmosphere valve assembly and the vacuum valve assembly from one of their first and second end stroke positions to the other of their end stroke positions.

In some aspects of the disclosure, the first and second biasing mechanisms each include an annular spring and an annular plate, wherein the annular spring is compressible and expandable to maintain the annular plate in engagement with a respective one of the frame members to maintain the atmosphere valve assembly and the vacuum valve assembly in its end stroke position as the piston shaft changes direction.

In certain aspects of the disclosure, an outer magnet is supported on the body adjacent each of the first and second fluid cavities of the first and second pump chambers, wherein the outer magnets are positioned to draw a respective one of the first and second pistons towards one of its end stroke positions when the fluid pump is stopped to facilitate restart of the fluid pump.

In another aspect of the disclosure, a fluid pump includes a body, a first diaphragm, a second diaphragm, a first piston, a second piston, an atmosphere valve assembly, a vacuum valve assembly, and outer magnets. The body defines a first pump chamber, a second pump chamber, a vacuum chamber, and an atmosphere channel. The vacuum chamber communicates with the vacuum source and the atmosphere channel communicates with atmosphere. The first diaphragm divides the first pump chamber into a first vacuum cavity and a first fluid cavity and the second diaphragm divides the second pump chamber into a second vacuum cavity and a second fluid cavity. The first piston is supported by the first diaphragm and the second piston is supported by the second diaphragm. The first piston is coupled to the second piston by a piston shaft such that the first and second pistons are movable in unison between first and second end stroke positions. The body defines a first bore that communicates the first vacuum cavity with the atmosphere channel, a second bore that communicates the second vacuum cavity with the atmosphere channel, a third bore that communicates the first vacuum cavity with the vacuum chamber, and a fourth bore that communicates the second vacuum cavity with the vacuum chamber. The atmosphere valve assembly includes a first valve member and a second valve member. The atmosphere valve assembly is movable between a first end stroke position in which the first valve member seals the first bore and the second bore is unsealed, and a second end stroke position in which the second seal member seals the second bore and the first bore is unsealed. The first valve member is coupled to the second valve member by a first valve shaft. The vacuum valve assembly includes a third valve member and a fourth valve member. The vacuum valve assembly is movable between a first end stroke position in which the third valve member seals the third bore and the fourth bore is unsealed, and a second end stroke position in which the fourth seal member seals the fourth bore and the third bore is unsealed. The third valve member is coupled to the fourth valve member by a second valve shaft. The outer magnets are supported on the body adjacent each of the first and second fluid cavities of the first and second pump chambers and are positioned to draw a respective one of the first and second pistons towards its end stroke position when the fluid pump is stopped to facilitate restart of the fluid pump.

BRIEF DESCRIPTION OF THE DRAWINGS

Various aspects of the disclosed vacuum assisted suction and irrigation systems are described herein below with reference to the drawings, wherein.

DETAILED DESCRIPTION

Figure 1:
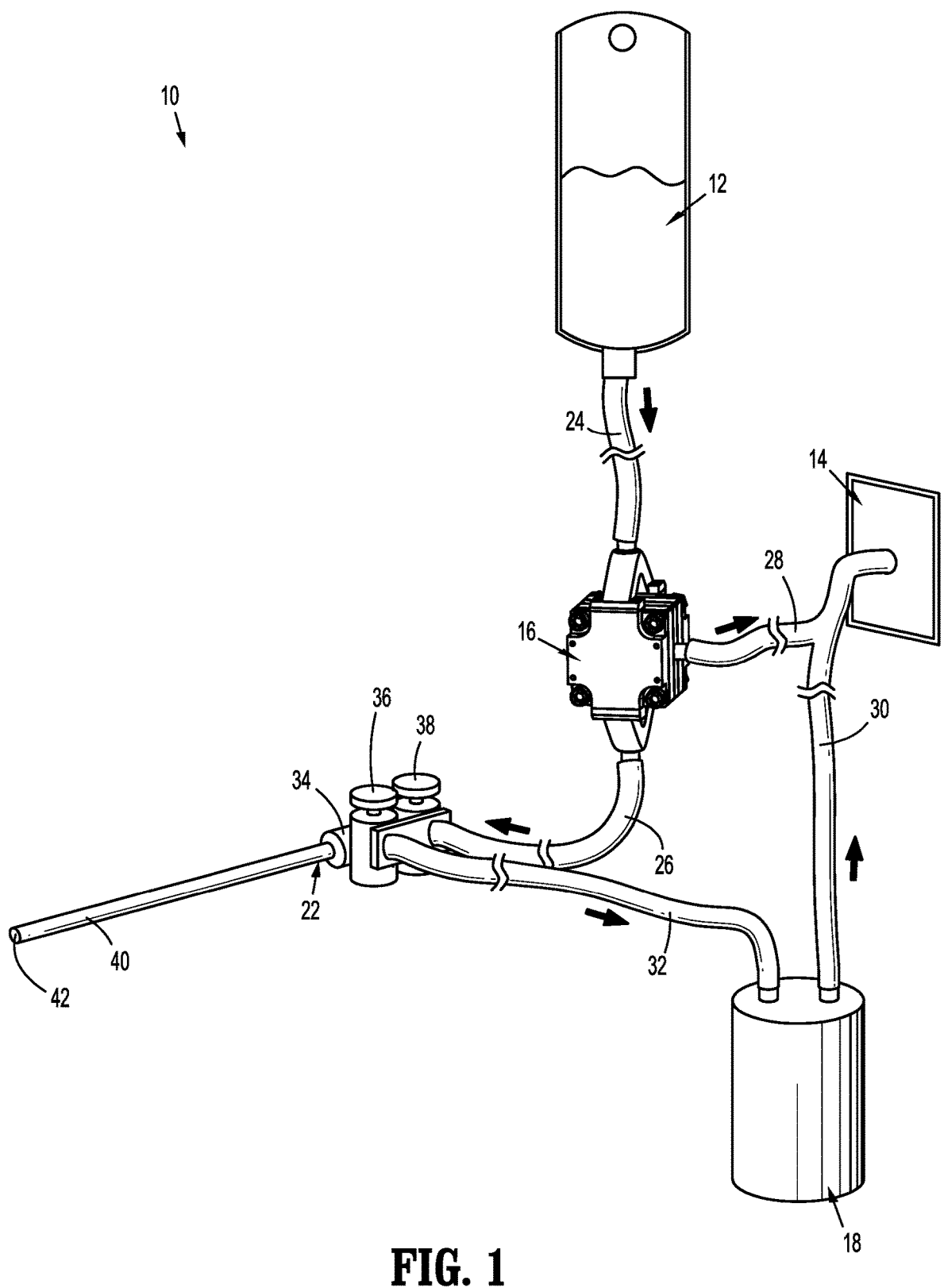
FIG. 1 is a side perspective cutaway view of exemplary aspects of the disclosed vacuum assisted suction and irrigation system.

Exemplary aspects of the disclosed vacuum assisted suction and irrigation system will now be described in detail with reference to the drawings in which like reference numerals designate identical or corresponding elements in each of the several views. However, it is to be understood that the disclosed aspects of the system are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

An exemplary aspect of the disclosed vacuum assisted suction and irrigation system is shown generally in FIG. 1 as system 10. The system 10 includes an irrigation fluid supply 12, a vacuum source 14, a fluid pump 16, a suction container 18, and a suction and irrigation wand 22. The components of the device 10 are fluidly coupled to each other with fluid conduits 24-32 as described in further detail below.

The suction and irrigation wand 22 includes a proximal body portion 34 and a distal body portion 40. The proximal body portion 34 supports a suction valve 36 and an irrigation valve 38. The distal body portion 40 defines a fluid channel 42 for receiving or dispensing fluid depending on which valve of the suction valve 36 and irrigation valve 38 is actuated. In aspects of the disclosure, the proximal body portion 34 of the suction and irrigation wand 22 is connected to the irrigation fluid supply 12 by the fluid conduits 24 and 26 such that upon actuation of the irrigation valve 38, irrigation fluid is delivered to the fluid channel 42 of the distal body portion 40 of the suction and irrigation wand 22. Similarly, the proximal body portion 34 of the suction and irrigation wand 22 is connected to the vacuum source 14 by the fluid conduits 30 and 32 via the suction container 18. Upon actuation of the suction valve 36, a vacuum is created in the fluid channel 42 of the distal body portion 40 of the suction and irrigation wand 22 to draw fluid into the fluid channel 42.

In some aspects of the disclosure, the suction and irrigation wand 22 communicates with the suction container 18 via the fluid conduit 32 and the suction container 18 communicates with the vacuum source 14 via the fluid conduit 30. As such, a vacuum is maintained within the suction container 18 by the vacuum source 14. Thus, when the suction valve 36 is actuated, the fluid channel 42 in the suction and irrigation wand 22 is communicates with the suction container 20 to create a vacuum within the fluid channel 42. All materials drawn into the channel 42 of the suction and irrigation wand 22, such as blood, tissue, saline, etc., are delivered to and collected within the suction container 20.

In some aspects of the disclosure, the irrigation supply 12 is coupled to the fluid pump 16 by fluid conduit 24 and the fluid pump 16 is coupled to the suction and irrigation wand 22 by the fluid conduit 26. When the irrigation valve 38 is actuated, fluid from within the irrigation fluid supply 12 is delivered to the suction and irrigation wand 22 via the fluid pump 16. In certain aspects of the disclosure, as described in further detail below, the irrigation fluid supply 12 can be connected directly to the suction and irrigation wand 22 and alternative means can be provided to pressurize the irrigation fluid supply 12.

Figure 2:
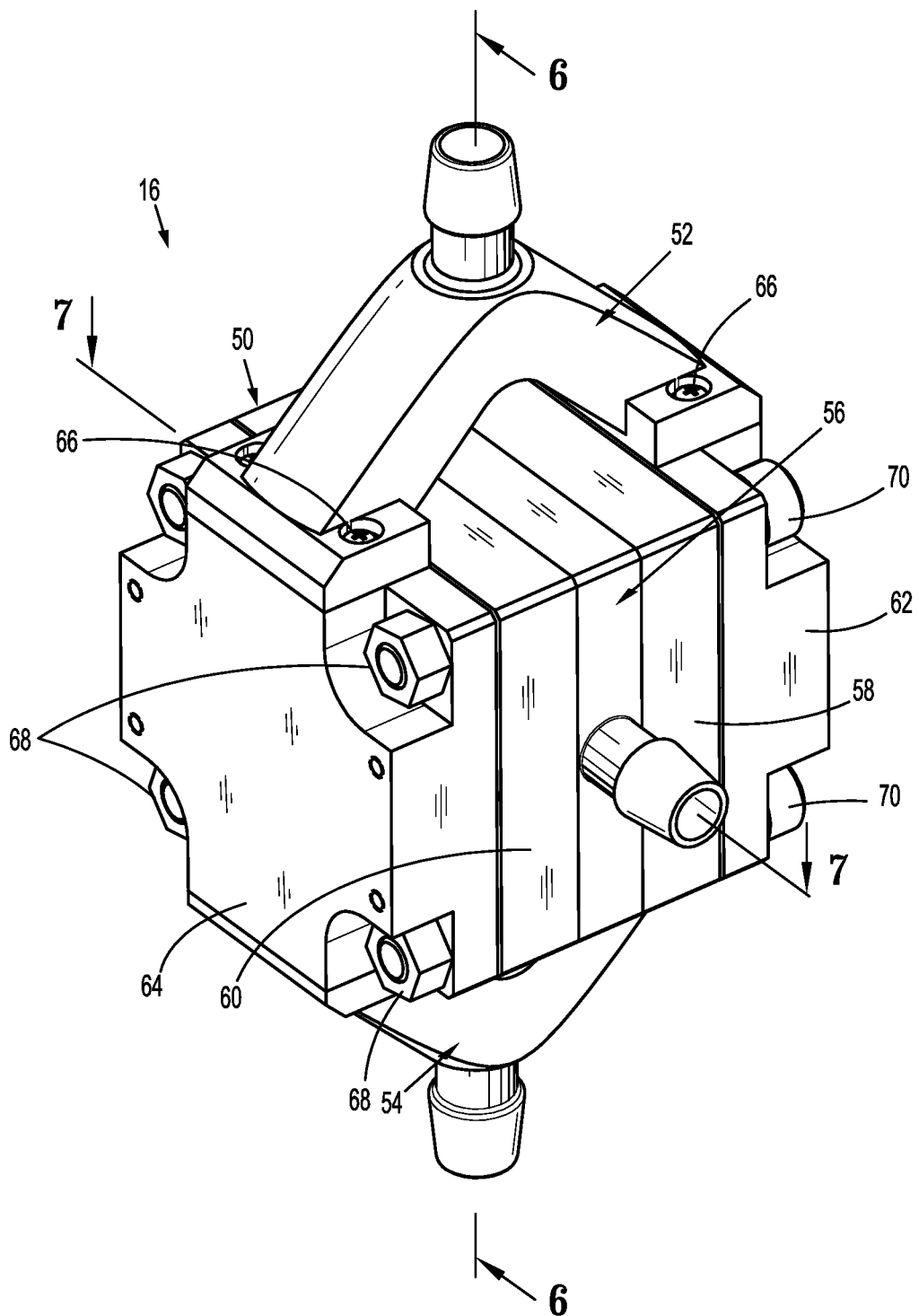
FIG. 2 is a side perspective view of a fluid pump of the vacuum assisted suction and irrigation system shown in FIG. 1.
Figure 3:
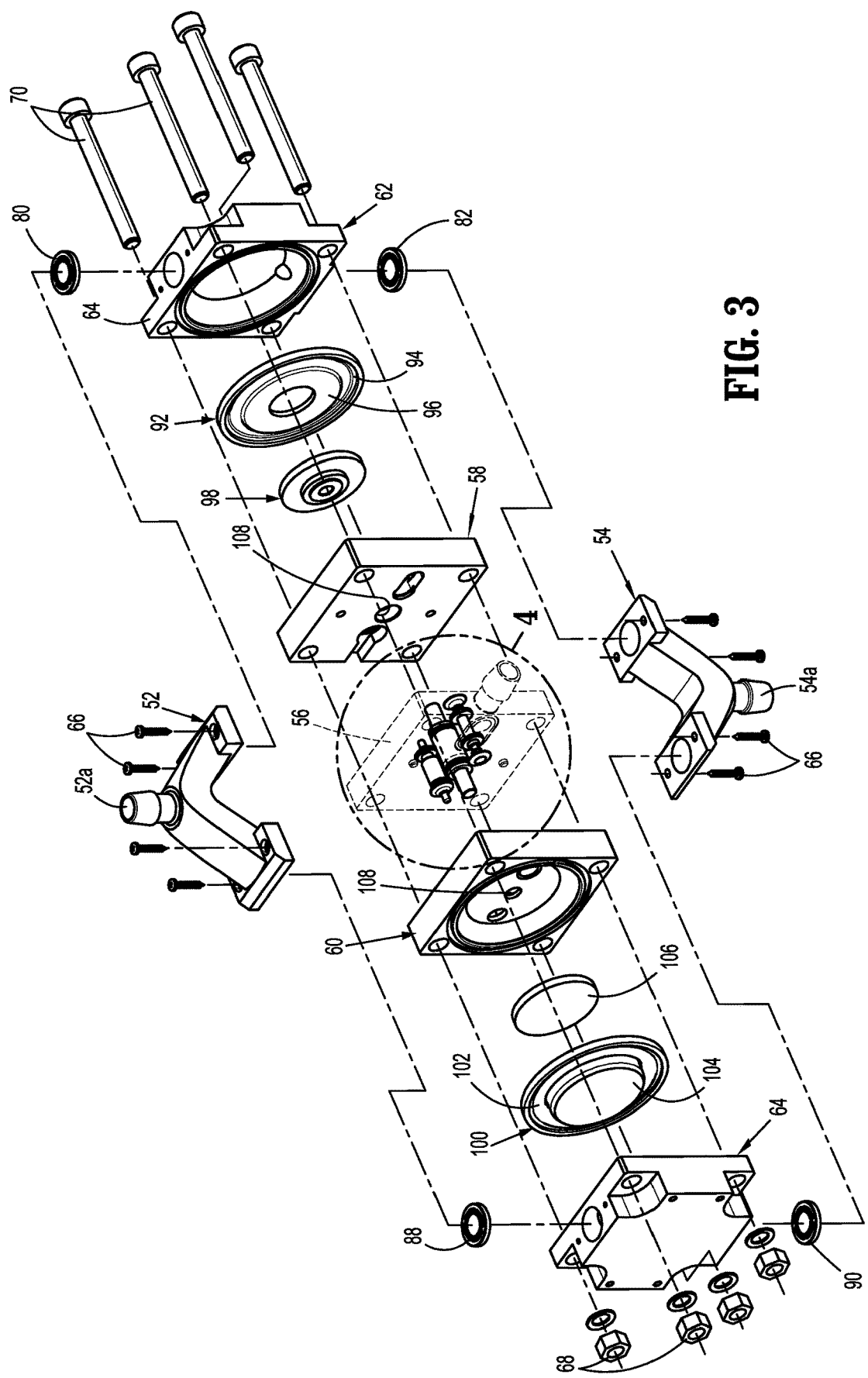
FIG. 3 is an exploded perspective view of the fluid pump of FIG. 2.
Figure 4:
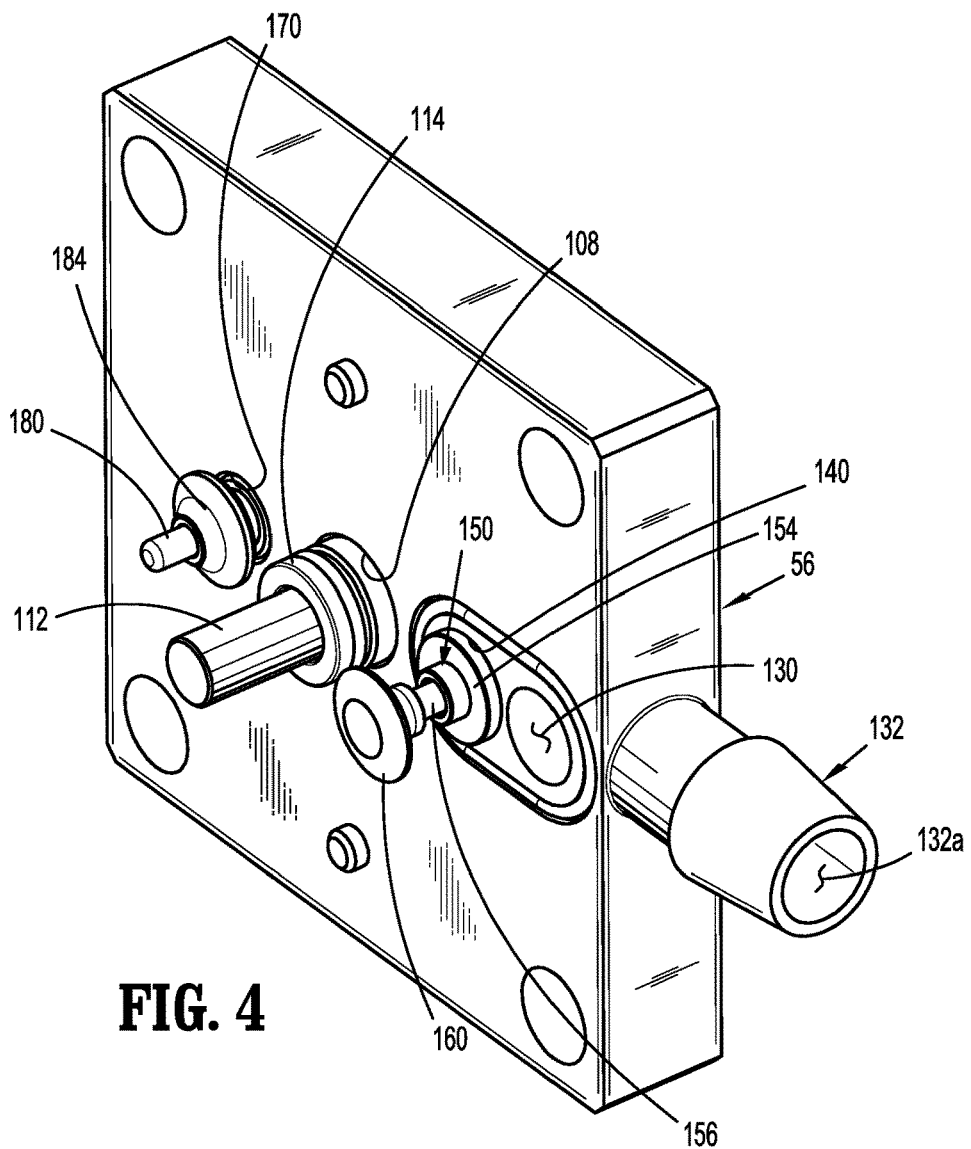
FIG. 4 is an enlarged view of the indicated area of detail shown in FIG. 3.

FIGS. 2-7 illustrate exemplary aspects of the fluid pump 16. Referring initially to FIG. 2, the fluid pump 16 is a diaphragm type pump and includes a housing 50, a fluid inlet manifold 52, and a fluid outlet manifold 54. The housing 50 includes a central housing portion 56, a first pump chamber body portion 58, a second pump chamber body portion 60, a first pump chamber cover 62, and a second pump chamber cover 64. The fluid inlet manifold 52 is coupled to the irrigation fluid supply 12 via the fluid conduit 24 (FIG. 1) and the fluid outlet manifold 54 is coupled to the suction and irrigation wand 22 via fluid conduit 26. In aspects of the disclosure, the fluid inlet and outlet manifolds 52, 54 can be secured to the housing 50 using screws 66 or the like. Similarly, the different components of the housing 50 can be secured together using nuts 68 and bolts 70 or the like.

Figure 5:
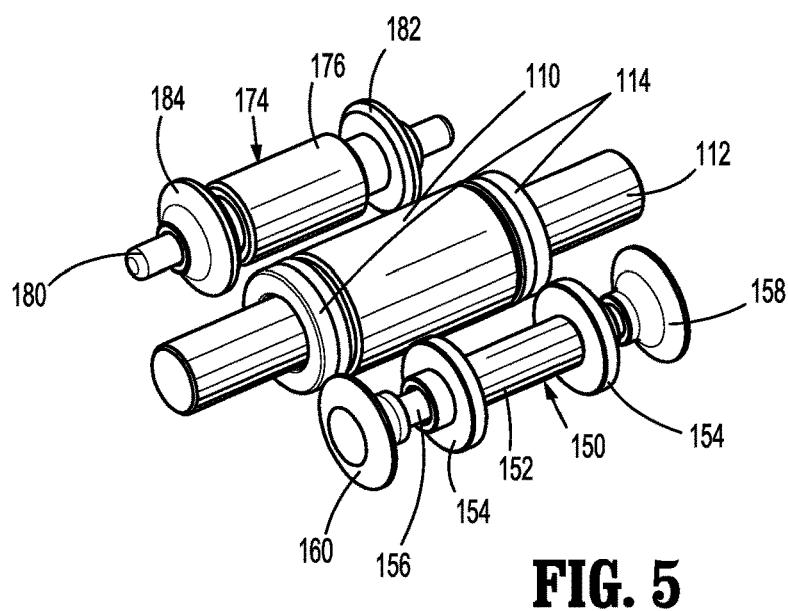
FIG. 5 is a side perspective view of a valve assembly of the fluid pump shown in FIG. 2.
Figure 6:
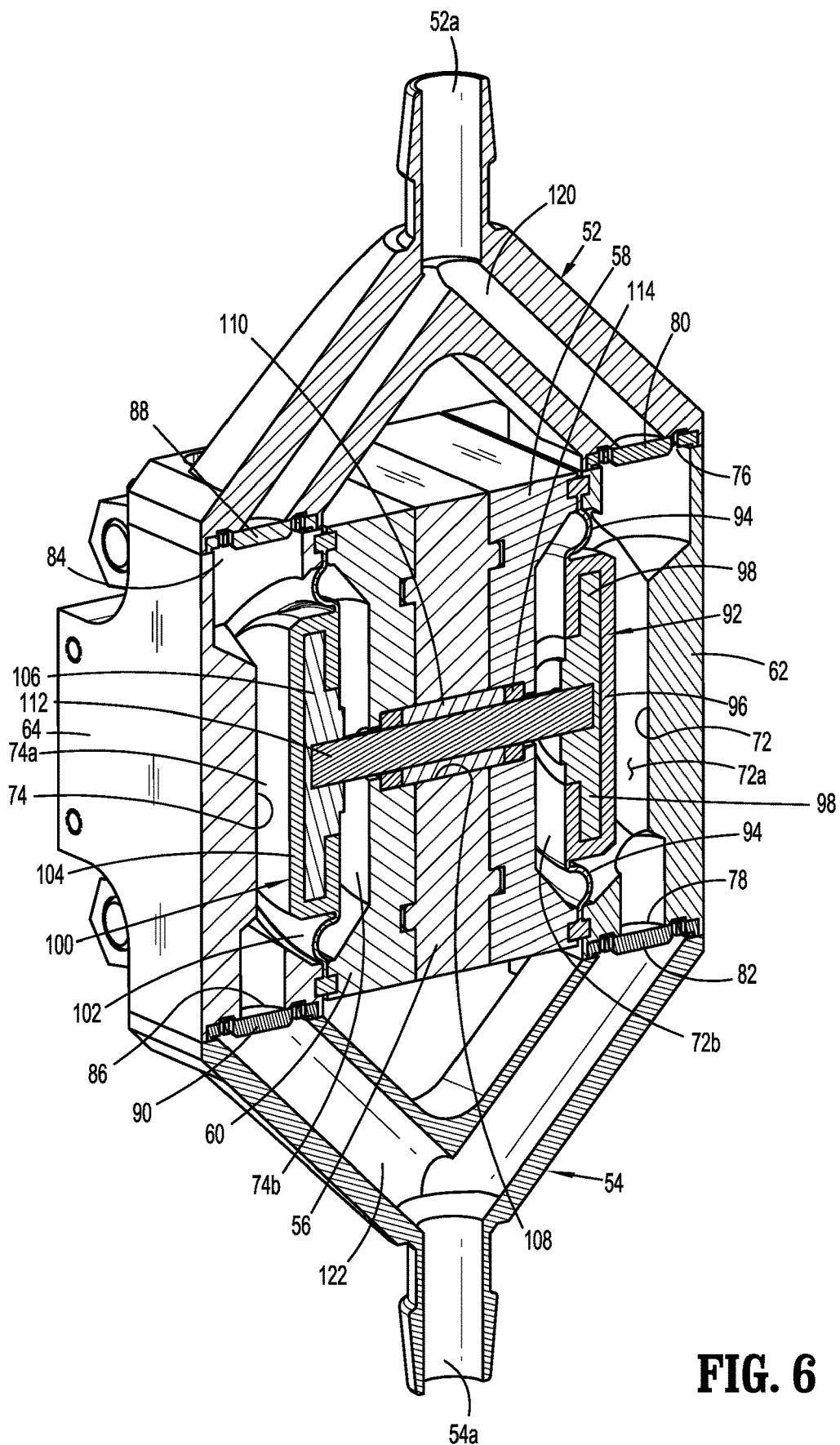
FIG. 6 is a cross-sectional view taken along section line 6-6 of FIG. 2.

Referring also to FIGS. 3-7, the fluid pump 16 includes two pump chambers 72, 74 (FIG. 6). The first pump chamber 72 is defined between the first pump chamber body portion 58 and the first pump chamber cover portion 62. The second pump chamber 74 is defined between the second pump chamber body portion 60 and the second pump chamber cover portion 64. The first pump chamber 72 defines an inlet opening 76 (FIG. 6) and a fluid outlet opening 78 (FIG. 6). Each of the inlet and outlet openings 76, 78, is sealed by a respective check valve 80, 82, respectively. Similarly, the second pump chamber 74 defines an inlet opening 84 and a fluid outlet opening 86 that are sealed by check valves 88, 90, respectively.

The first pump chamber 72 is divided into a fluid cavity 72a and a vacuum cavity 72b by a diaphragm 92 (FIG. 6). In some aspects of the disclosure, the diaphragm 92 includes an outer flexible portion 94 of reduced thickness and a more rigid central portion 96 that is configured to support a first piston 98. Similarly, the second pump chamber 74 is divided into a fluid cavity 74a and a vacuum cavity 74b by a diaphragm 100 (FIG. 6). Similarly, in some aspects of the disclosure, the diaphragm 100 includes an outer flexible portion 102 of reduced thickness and a more rigid central portion 104 that is configured to support a second piston 106.

The central housing portion 56 and the body portions 58, 60 of the housing 50 define a bore 108 (FIG. 6) that that extends between the first and second pump chambers 72, 74, respectively. The bore 108 receives a bushing 110 and a piston shaft 112 that has a first end secured to the first piston 98 and a second end secured to the second piston 106. As such, movement of the first piston 98 within the first pump chamber 72 causes corresponding movement of the second piston 106 within the second pump chamber 74. A seal 114 is supported about the piston shaft 112 at each end of the bushing 110 to provide a seal about the piston shaft 112 within the bore 108 at each end piston shaft 112.

Referring briefly to FIG. 6, the inlet manifold 52 defines a bifurcated or Y-shaped fluid channel 120 having an inlet 52a that communicates with the inlet openings 76, 84 of the first and second pump chambers 72, 74, respectively. The outlet manifold 54 defines a Y-shaped fluid channel 122 that has an outlet 54a that communicates with the outlet openings 78, 86 of the first and second pump chambers 72, 74, respectively. The check valves 80, 82, 88 and 90 are configured to allow fluid to flow in one direction, i.e., into the first and second pump chambers 72, 74 from the inlet manifold 52 and out of the first and second pump chambers 72, 74 through the outlet manifold 54.

Figure 7:
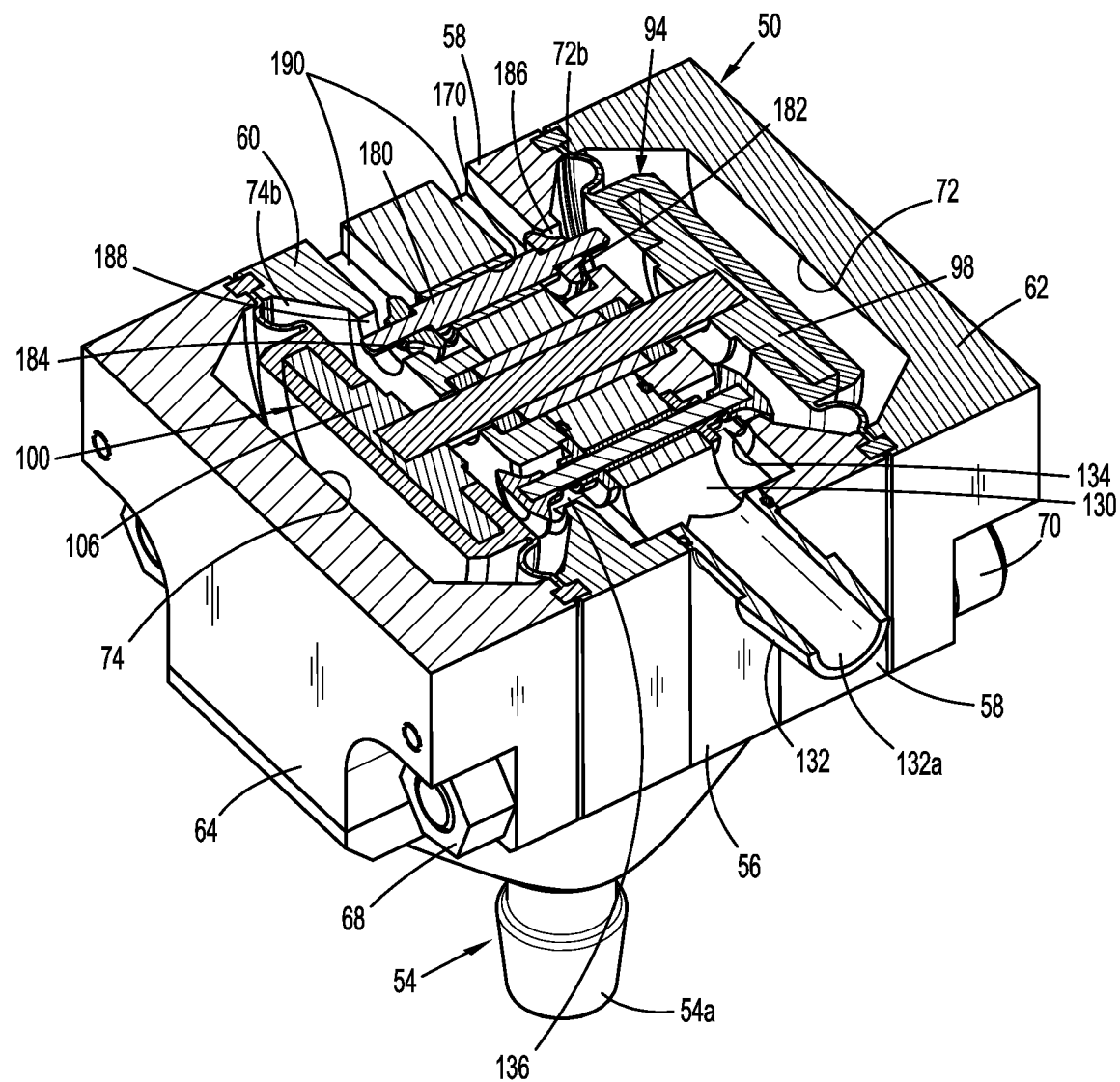
FIG. 7 is a cross-sectional view taken along section line 7-7 of FIG. 2.

FIGS. 3-7 illustrate the central housing portion 56 and the first and second pump chamber body portions 58, 60 of the housing 50 of the fluid pump 16 which define a vacuum chamber 130 and a vacuum port 132 (FIG. 7). The vacuum port 132 defines a channel 132a that communicates with the vacuum chamber 130. The first pump chamber body portion 58 defines a bore 134 (FIG. 8) that communicates the vacuum chamber 130 with the vacuum cavity 72b of the first pump chamber 72. Similarly, the second pump chamber body portion 60 defines a bore 136 that communicates the vacuum chamber 130 with the vacuum cavity 74b of the second pump chamber 74. The bores 134, 136 are positioned to facilitate application of a vacuum to the vacuum cavities 72b, 74b of the first and second pump chambers 72, 74 of the fluid pump 16 to control movement of the diaphragms 94, 100 within the first and second pump chambers 72, 74 as described in more detail below.

The central housing portion 56 (FIG. 4) of the housing 50 of the fluid pump 16 defines a bore 140 that receives a vacuum valve assembly 150. The vacuum valve assembly 150 includes a bushing 152, first and second seal members 154, a valve shaft 156, and valve members 158, 160 that are positioned to alternately seal the bores 134, 136 of the first and second pump chamber body portions 58, 60 (FIG. 5). The valve shaft 156 connects the valve member 158 to the valve member 160 and is movable between a first position in which the valve member 158 seals the bore 134 of the first pump chamber body portion 58 while the bore 136 of the second pump chamber body portion 60 remains unsealed and a second position in which the valve member 160 seals the bore 136 of the second pump chamber body portion 60 while the bore 134 of the first pump chamber body portion 58 remains unsealed. The first and second seal members 154 provide a seal about the valve shaft 156 at each end of the bore 140 of the central housing portion 56 to prevent fluid leakage between the first and second pump chambers 72, 74.

The central housing portion 56 of the housing 50 of the fluid pump 16 also defines a bore 170 (FIG. 4) that receives an atmosphere valve assembly 174. The first and second pump chamber body portions 58, 60 define bores 186, 188.

The atmosphere valve assembly 174 includes a bushing 176, a valve shaft 180, and valve members 182, 184 that are positioned to alternately seal the bores 186, 188. The bores 186, 188 connect the vacuum cavities 72b, 74b of the first and second pump chambers 72, 74 with atmosphere channels 190 (FIG. 7) formed in the first and second pump chamber body portions 58, 60. The valve shaft 180 connects the valve member 182 to the valve member 184 and is movable within the bushing 176 between a first position in which the valve member 182 seals the bore 186 of the first pump chamber body portion 58 while the bore 188 of the second pump chamber body portion 60 remains unsealed and a second position in which the valve member 184 seals the bore 188 of the second pump chamber body portion 60 while the bore 186 of the first pump chamber body portion 58 remains unsealed.

Figure 8:
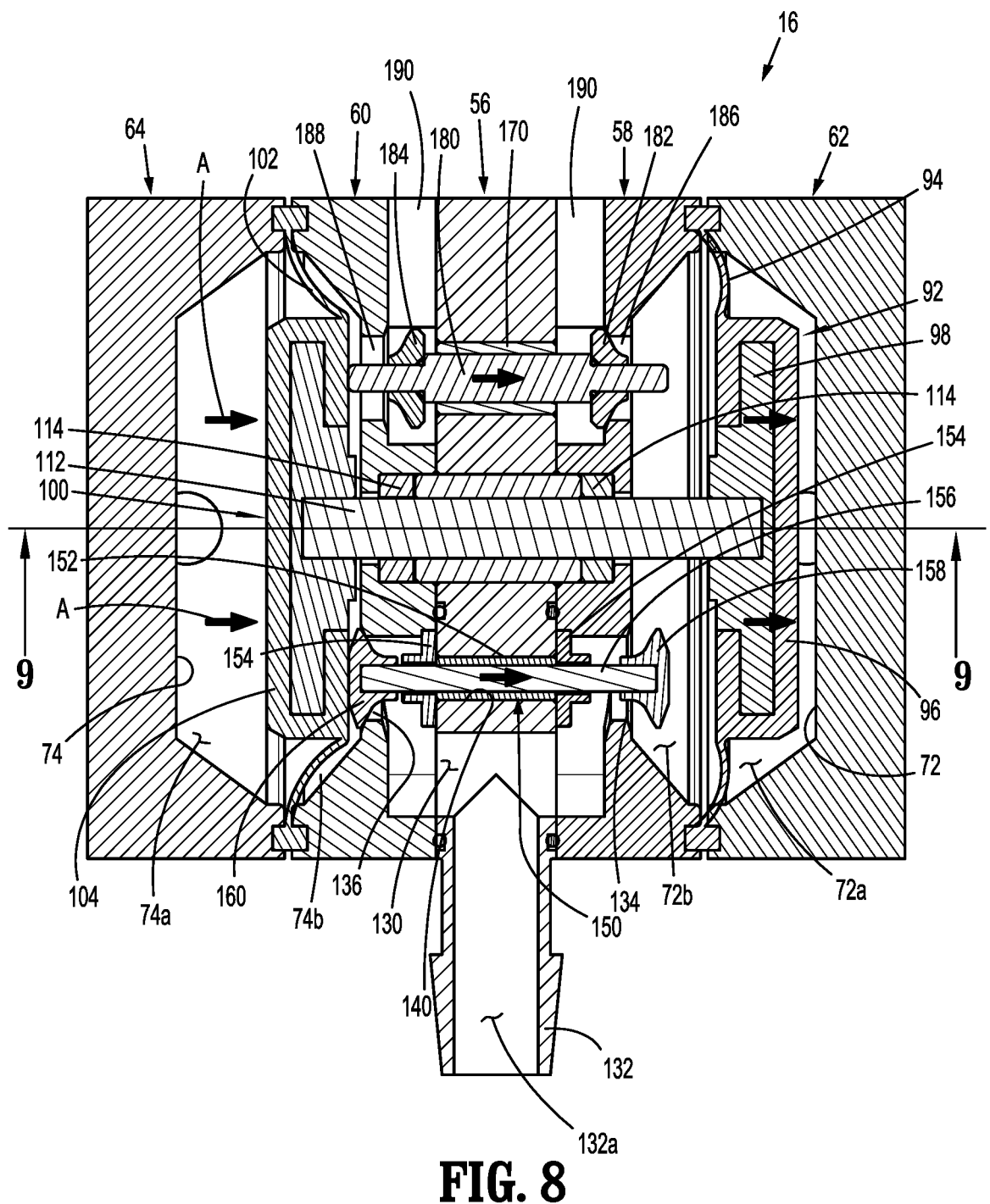
FIG. 8 is a side cross-sectional view of the of the fluid pump shown in FIG. 2 as fluid is pumped from a first pump chamber of the fluid pump.
Figure 9:
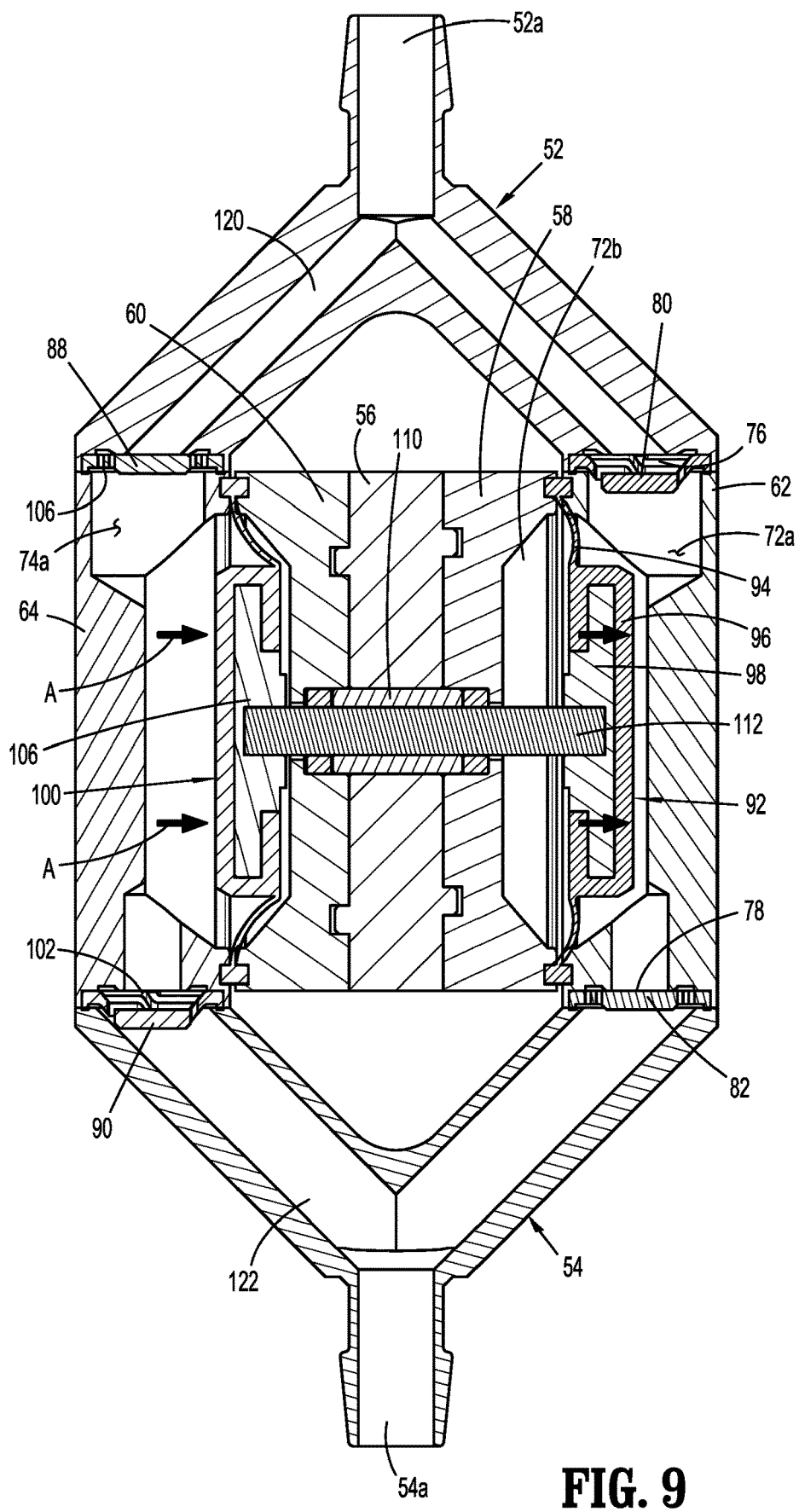
FIG. 9 is a cross-sectional view taken along section line 9-9 of FIG. 8.

FIGS. 8 and 9 illustrate the valve shaft 180 of the atmosphere valve assembly 174 and the valve member 160 of the vacuum valve assembly 150 which are positioned to be engaged by the diaphragm 104 within the second pump chamber 74 when the diaphragm 104 moves in the direction indicated by arrows "A" to a position to collapse the vacuum cavity 74b of the second pump chamber 74. As the diaphragm 104 moves to the position shown in FIG. 8 in the direction of arrow "A", the valve member 184 of the atmosphere valve assembly 174 moves to a position to unseal the bore 188 connecting the vacuum cavity 74b of the second pump chamber 74 to the atmosphere channels 190 and the valve member 182 moves to a position to seal the bore 186 connecting the vacuum cavity 72b of the first pump chamber 72 to the atmosphere channels 190. Similarly, as the diaphragm 104 moves to the position shown in FIG. 8, the valve shaft 156 of the vacuum valve assembly 150 moves in the direction of arrows "A" to move the valve member 160 of the vacuum valve assembly 150 to a position to seal the bore 136 connecting the vacuum chamber 130 to the vacuum cavity 74b and the valve member 158 moves to a position to unseal the bore 134 connecting the vacuum chamber 130 to the vacuum cavity 72b of the first pump chamber 72. As the diaphragm 100 moves to the position in which the vacuum chamber 74b is collapsed, the fluid cavity 74a of the second pump chamber 74 is expanded to draw fluid into the fluid cavity 74a through the check valve 88. As the diaphragm 94 in the first pump chamber 72 moves in the direction indicated by arrows "A", irrigation fluid is forced from the fluid cavity 72a of the first pump chamber 72 through the check valve 82 and into the fluid outlet manifold 54.

Figure 10:
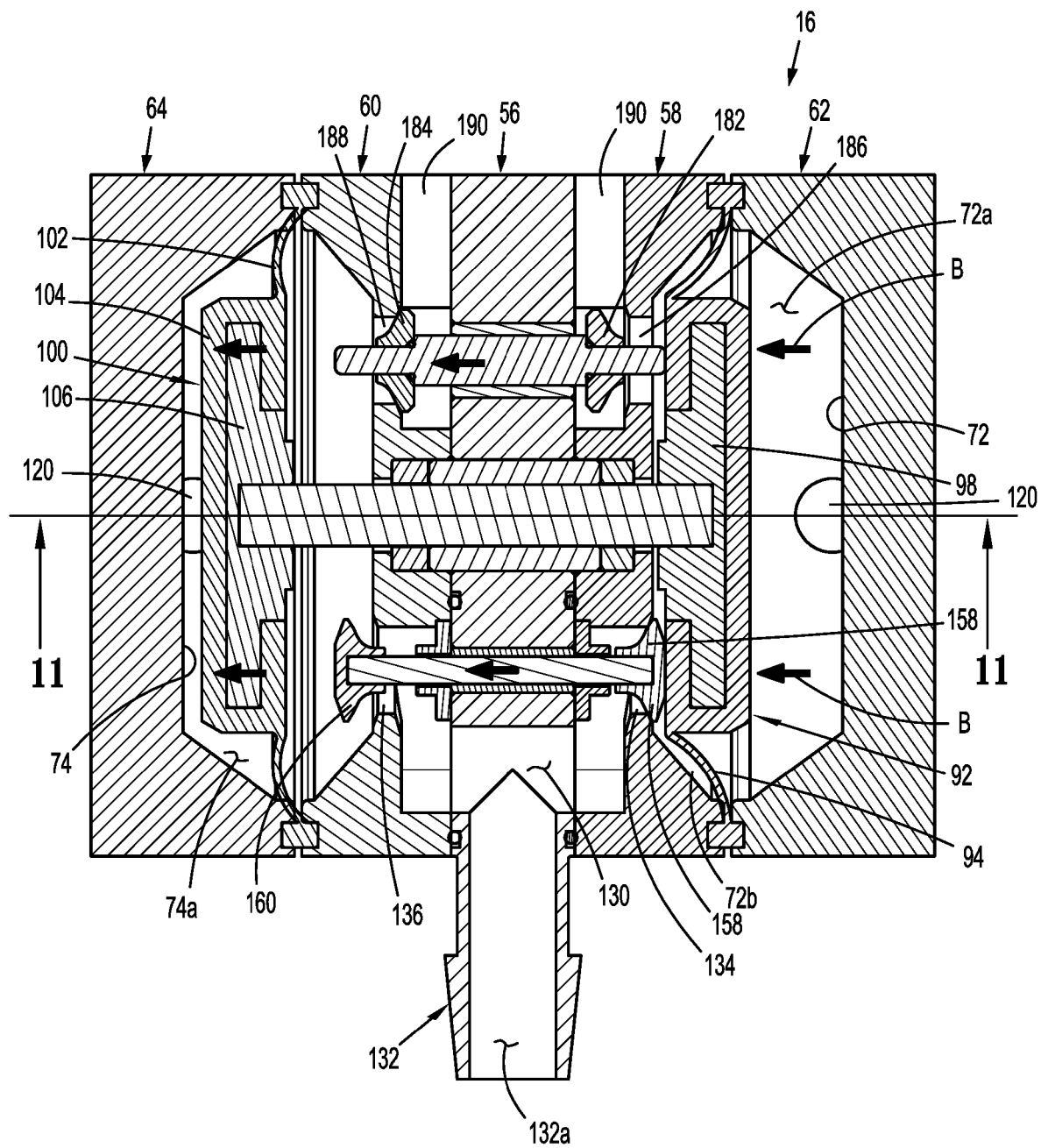
FIG. 10 is a side cross-sectional view of the fluid pump shown in FIG. 2 as fluid is pumped from a second pump chamber of the fluid pump.
Figure 11:
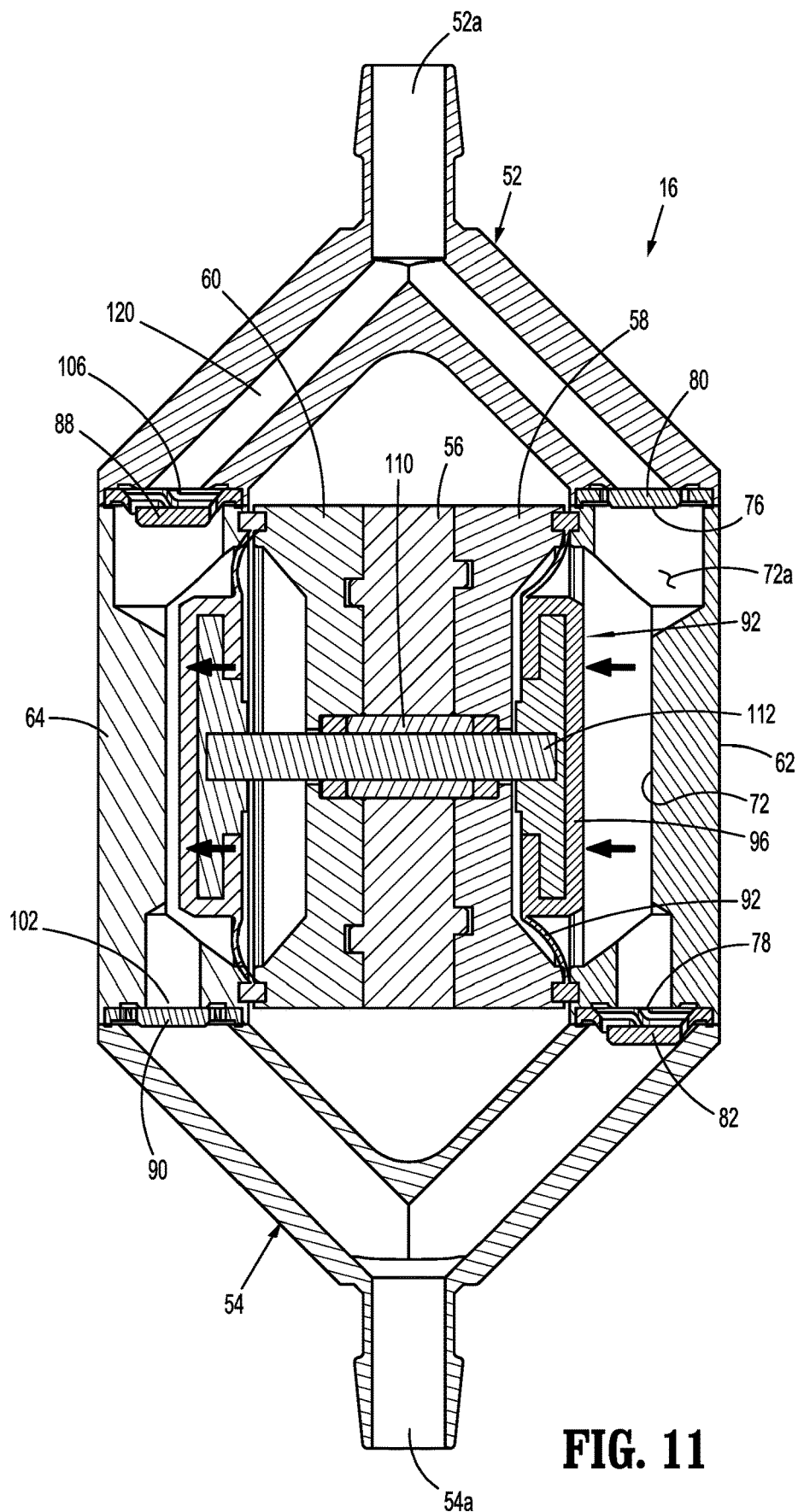
FIG. 11 is a cross-sectional view taken along section line 11-11 of FIG. 10.

FIGS. 10 and 11 illustrate the valve members 158 and 184 (FIG. 8) as the valve member 158 unseals the bore 134 and the valve member 184 unseals the bore 188. When this occurs, a vacuum is drawn in the vacuum cavity 72b of the first pump chamber 72 and the vacuum cavity 74b of the second pump chamber 74 is vented. This creates a pressure differential between the vacuum cavities 72b, 74b of the first and second pump chambers 72, 74, which causes the diaphragm 92 in the first pump chamber 72 to move in the direction of arrows "B" in FIGS. 10 and 11 to collapse the vacuum cavity 72b of the first pump chamber 72. As the vacuum cavity 72b collapses, the fluid cavity 72a of the first pump chamber 72 expands to draw irrigation fluid into the fluid cavity 72a through the first check valve 80 (FIG. 11). As the diaphragm 94 moves in the direction indicated by arrows "B" in FIG. 10 to move the piston shaft 112 in the direction of arrow "B", the piston shaft 112 causes corresponding movement of the diaphragm 100 within the second pump chamber 74 to force irrigation fluid from the fluid cavity 74a of the second pump chamber 74 through the check valve 90 (FIG. 11). Movement of the diaphragm 100 also causes expansion of the vacuum cavity 74b of the second pump chamber 74.

Similar to diaphragm 104, the diaphragm 94 is positioned to engage the valve shaft 180 of the atmosphere valve assembly 174 and the valve member 158 of the vacuum valve assembly 150 when the diaphragm 94 moves in the direction indicated by arrows "B" to unseal the bore 130 connecting the vacuum chamber 74b of the second pump chamber 74 to the vacuum chamber 130 and to unseal the bore 186 connecting the vacuum cavity 72b of the first pump chamber 72. Once again, this pressure differential within the vacuum cavities 72b, 74b of the first and second pump chambers 72, 74 causes the diaphragm 94 to change direction and move in the direction of arrow "A" (FIG. 8). The diaphragms 94 and 100 will continue to operate in this manner to provide a pressurized supply of irrigation fluid to the irrigation and suction wand 22 (FIG. 1).

Figure 12:
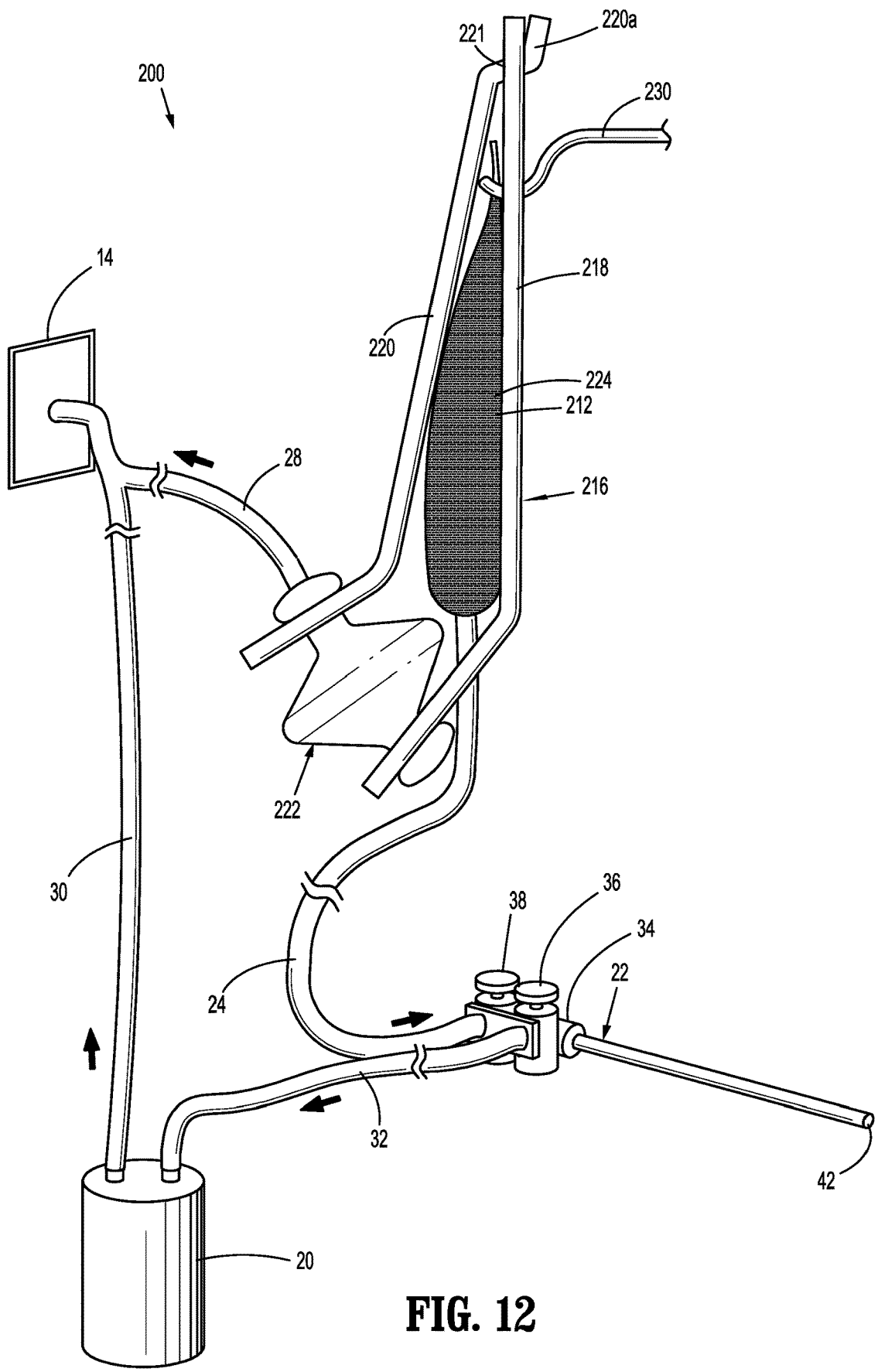
FIG. 12 a side perspective, schematic view of another exemplary aspect of the disclosed vacuum assisted suction and irrigation system.
Figure 13:
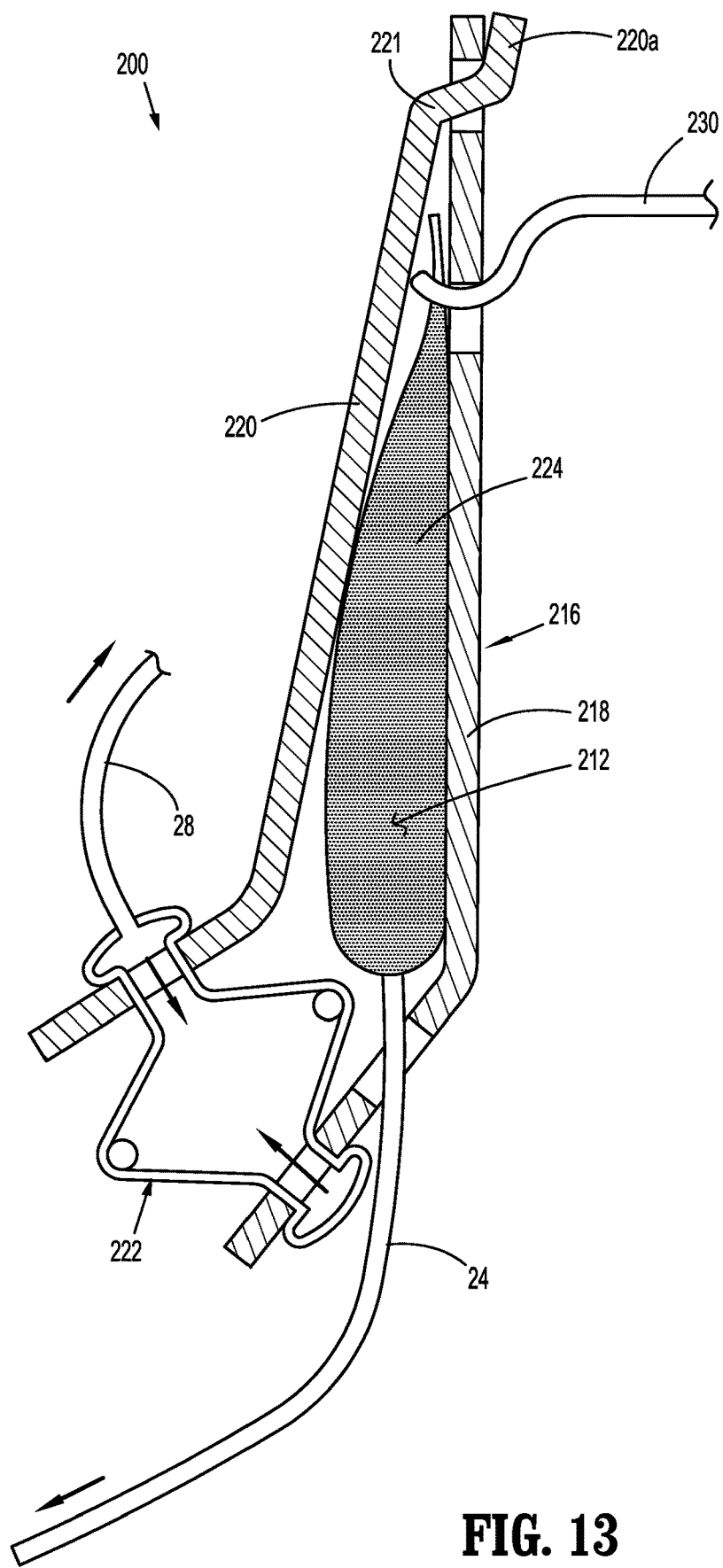
FIG. 13 is a side cross-sectional view of the fluid pump of the vacuum assisted suction and irrigation system shown in FIG. 12.
Figure 15:
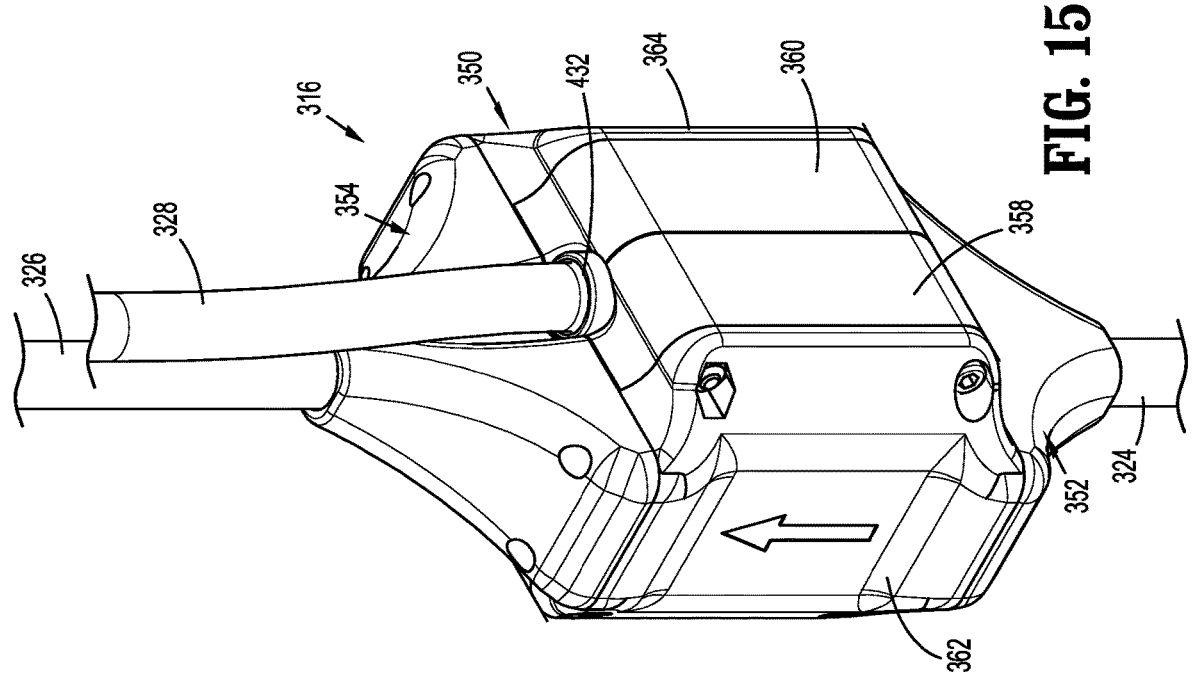
FIG. 15 is a side perspective view from a second end of the fluid pump shown in FIG. 14.

FIGS. 12 and 13 illustrate an alternate suction and irrigation system shown generally as 200 that includes an alternative fluid pump shown generally as fluid pump 216. In the suction and irrigation system 200, the fluid pump 216 includes a base member 218, a compression member 220, and a bellows 222. The compression member 220 has a first end 220a that is pivotally supported on the base member 218 by a pivot member 221 which may have a variety of configurations. The irrigation fluid supply 212 includes a compressible pouch 224 that defines a receptacle that receives irrigation fluid. The compressible pouch 224 is supported between the base member 218 and the compression member 220. In aspects of the disclosure, the compressible pouch 224 is supported on a hook member 230 that also supports the base member 218. Alternately, the compressible pouch 224 can be supported on the base member 218 using a hook or other type of coupling member.

The bellows 222 is secured to ends of the base member 218 and the compression member 220 opposite the pivot member 221. The bellows 222 is movable between contracted and expanded configurations to pivot the compression member 220 in relation to the base member 218 to pressurize the irrigation fluid within the compressible pouch 224. In aspects of the disclosure, the bellows 222 is connected to the vacuum source 14 by a fluid conduit 28 to control expansion and contraction of the bellows 222. In aspects of the disclosure, the pressure within the bellows 222 is controlled with the vacuum source 12 to maintain the pressure of the irrigation fluid within the compressible pouch 224 constant.

The vacuum assisted suction and irrigation systems 10 and 200 operate in substantially similar manners. More specifically, a clinician grasps the proximal body portion 34 of the suction and irrigation wand 22 and manipulates the wand to position a distal end of the distal body portion 40 adjacent a surgical site (not shown). Although not shown, this may include inserting the distal body portion 40 of the suction and irrigation wand 22 through a cannula assembly to access a surgical site. If the clinician requires suction at the surgical site, e.g., to remove blood or debris, the clinician can actuate the suction valve 36 to draw material from the surgical site into the channel 42 of the suction and irrigation wand 22. All material withdrawn into the suction and irrigation wand 22 is delivered to the suction container 20 via the fluid conduit 32. If the clinician requires irrigation fluid, e.g., to improve visualization of the surgical site, the clinician can actuate the irrigation valve 38 to deliver fluid to the channel 42 of the distal body portion 40 of the suction and irrigation wand 22. In both systems, vacuum from the vacuum source 14 assists in pressurizing the irrigation fluid to supply the irrigation fluid to the suction and irrigation wand 22.

FIGS. 14-21 illustrate an alternate fluid pump shown generally as fluid pump 316 suitable for use with the disclosed vacuum assisted suction and irrigation system (FIG. 1). The fluid pump 316 includes a housing 350, a fluid inlet manifold 352, and a fluid outlet manifold 354. The housing 350 includes a central housing portion 356 (FIG. 16), a first body portion 358, a second body portion 360, a first cover 362, and a second cover 364. The fluid inlet manifold 352 is coupled to the irrigation fluid supply 12 (FIG. 1) via a fluid conduit 324 and the fluid outlet manifold 354 is coupled to the suction and irrigation wand 22 (FIG. 1) via a fluid conduit 326. In some aspects of the disclosure, the fluid inlet and outlet manifolds 352, 354 can be secured to the housing 350 using screws 366 (FIG. 16) and the components of the housing 350 can be secured together using nuts 368 and bolts 370.

Figure 18:
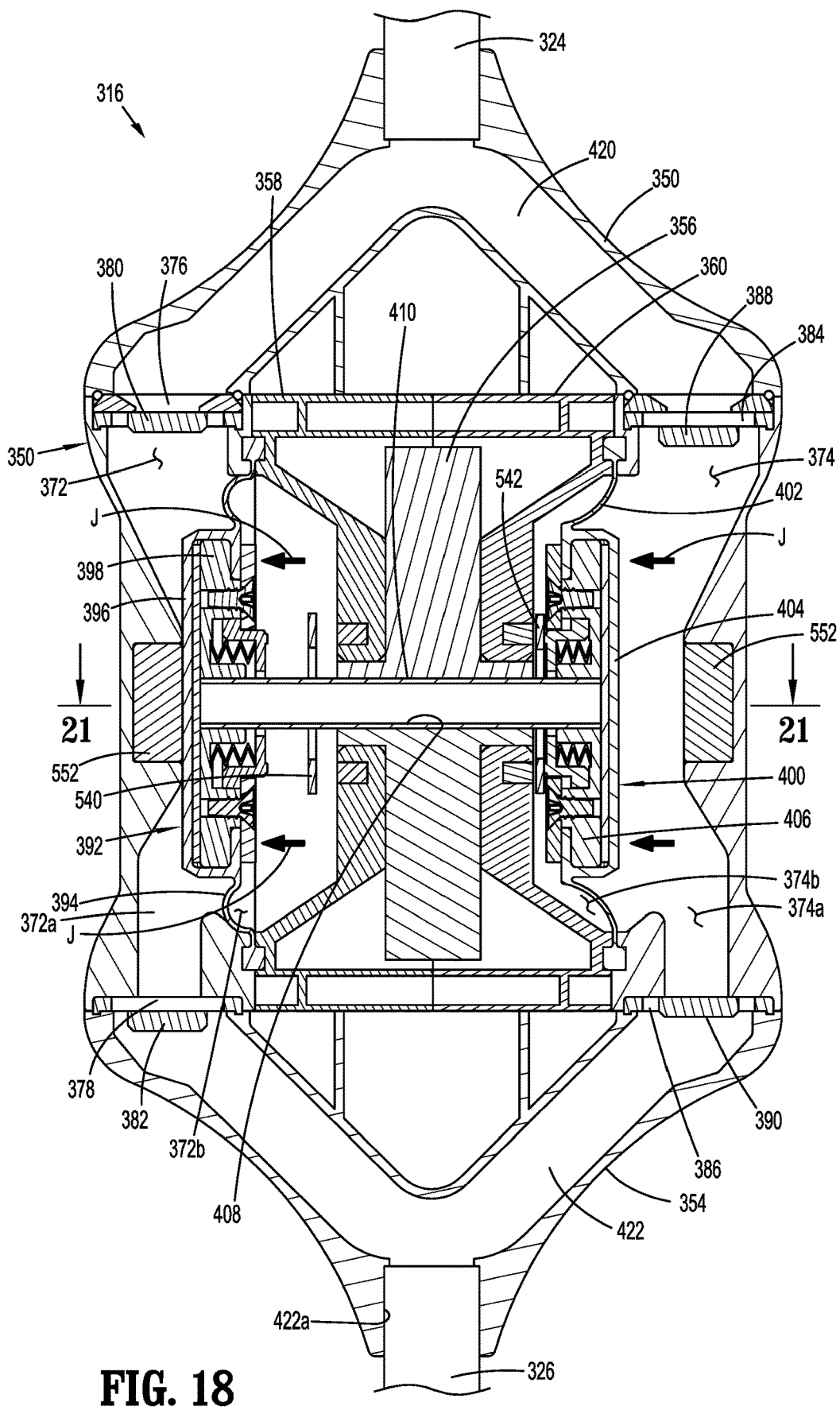
FIG. 18 is a cross-sectional view taken along section line 18-18 of FIG. 14 with a piston shaft of the fluid pump in a first position.
Figure 20:
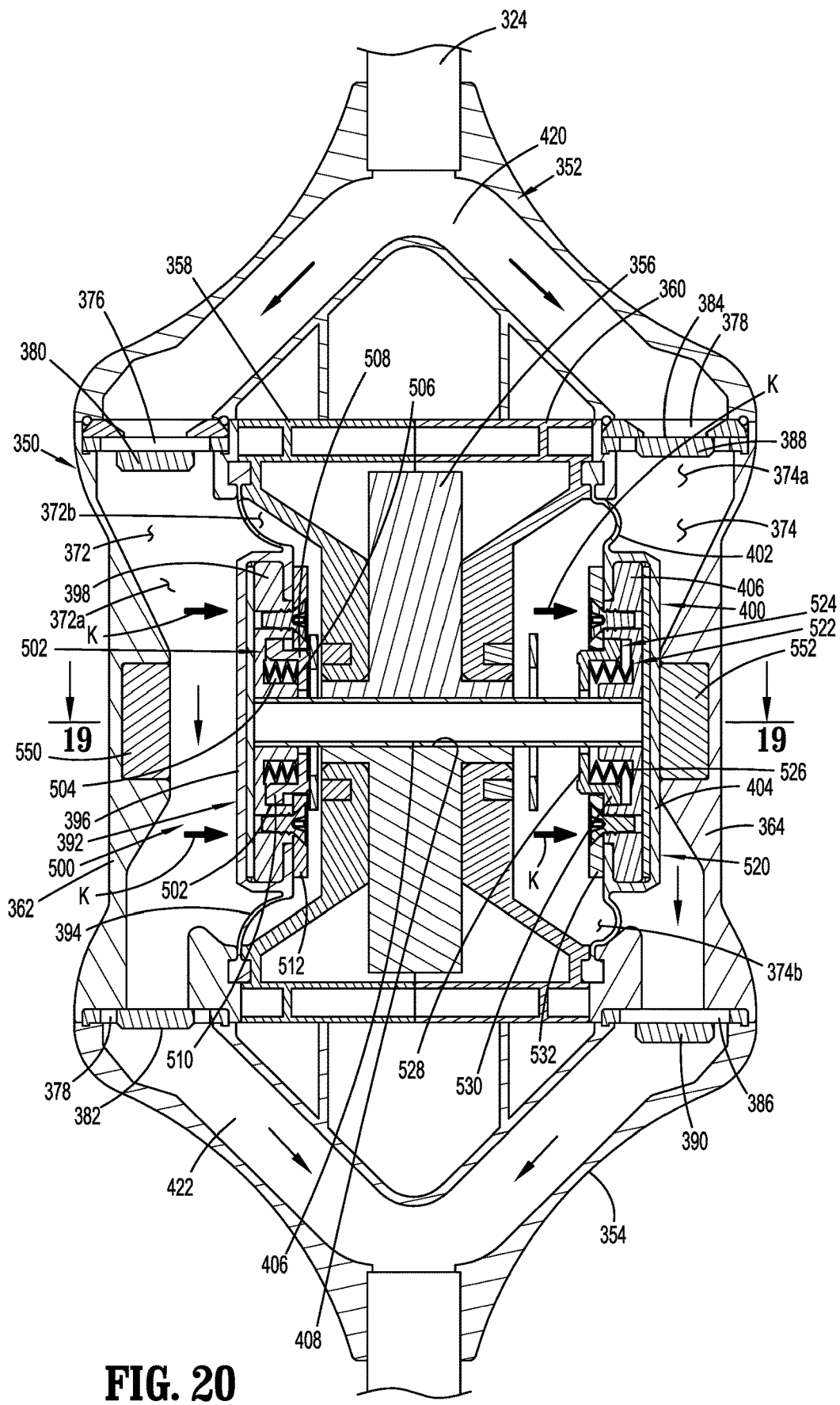
FIG. 20 is a cross-sectional view taken along section line 18-18 of FIG. 14 with the piston shaft of the fluid pump in a second position.

The housing 350 of the fluid pump 316 defines two pump chambers 372, 374 (FIG. 18). The first pump chamber 372 is defined between the first body portion 358 and the first cover portion 362 and the second pump chamber 374 is defined between the second body portion 360 and the second cover portion 364. The first pump chamber 372 defines an inlet opening 376 (FIG. 18) and a fluid outlet opening 378 (FIG. 20). Each of the inlet and outlet openings 376, 378 is sealed by a check valve 380, 382, respectively. Similarly, the second pump chamber 374 defines a fluid inlet opening 384 and a fluid outlet opening 386 which are sealed by check valves 388, 390, respectively.

The first pump chamber 372 is divided into a fluid cavity 372a and a vacuum cavity 372b by a diaphragm 392. The diaphragm 392 includes an outer flexible portion 394 of reduced thickness and a central more rigid portion 396 that is configured to support a first piston or shaft holder 398. The second pump chamber 374 is also divided into a fluid cavity 374a and a vacuum cavity 374b by a diaphragm 400. The diaphragm 400 includes an outer flexible portion 402 of reduced thickness and a central more rigid portion 404 that is configured to support a piston or shaft holder 406.

In aspects of the disclosure, the central housing portion 356 of the housing 350 defines a bore 408 (FIG. 19) that that extends between the first and second pump chambers 372, 374, respectively. The bore 408 receives a piston shaft 410 that has a first end secured to the shaft holder 398 and a second end secured to the shaft holder 406. As such, movement of the first shaft holder 398 within the first pump chamber 372 causes corresponding movement of the shaft holder 406 within the second pump chamber 374.

FIG. 18 illustrates a cross-sectional view of the fluid pump 316. As shown, the inlet manifold 352 defines a bifurcated or Y-shaped fluid channel 420 that communicates with the inlet openings 376, 384 of the first and second pump chambers 372, 374, respectively. The outlet manifold 354 also defines a Y-shaped fluid channel 422 that has an outlet 422a that communicates with the outlet openings 378, 386 of the first and second pump chambers 372, 374, respectively. The check valves 380, 382, 388, and 390 are configured to allow fluid to flow through the housing 350 of the fluid pump 316 in one direction, i.e., into the first and second pump chambers 372, 374 from the inlet manifold 352 and out of the first and second pump chambers 372, 374 through the outlet manifold 354.

Figure 14:
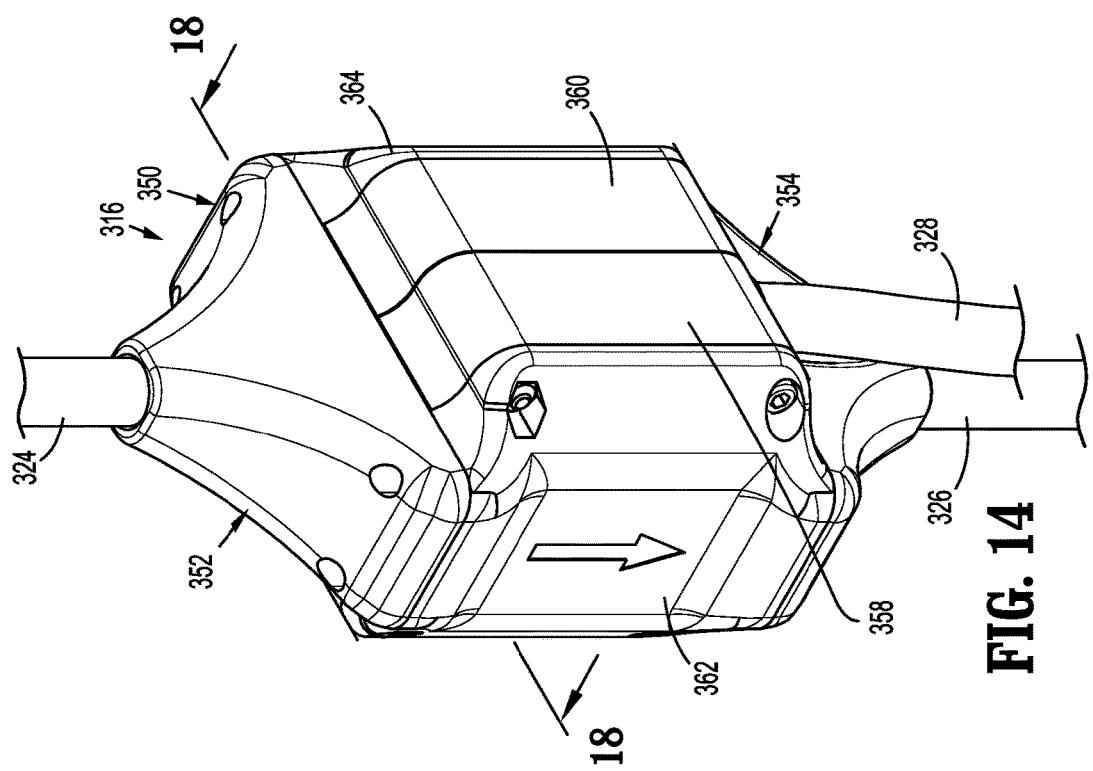
FIG. 14 is a side perspective view from a first end of an alternate fluid pump of the vacuum assisted suction and irrigation system shown in FIG. 1.
Figure 16:
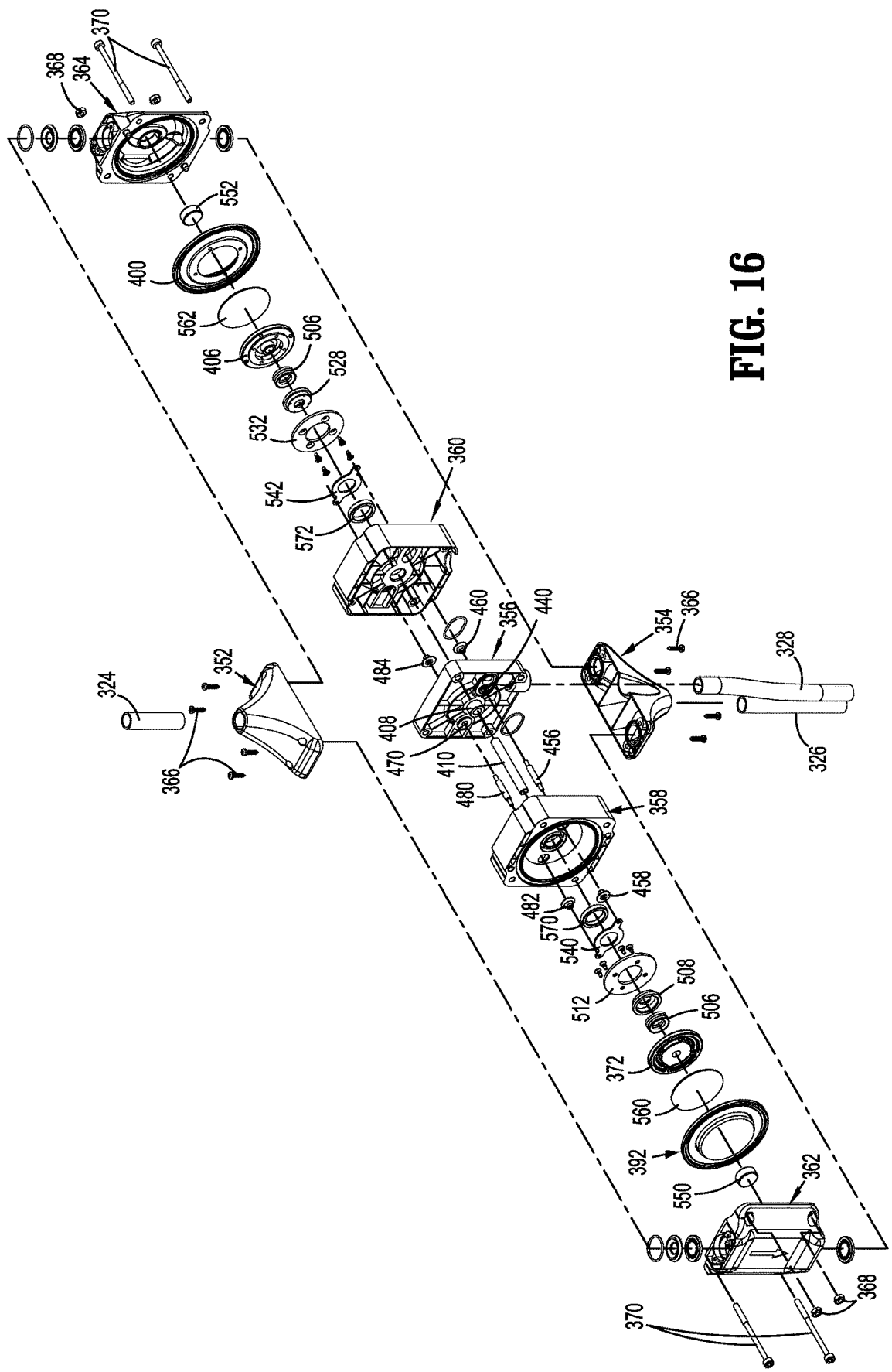
FIG. 16 is an exploded side perspective view of the fluid pump shown in FIG. 15.
Figure 17:
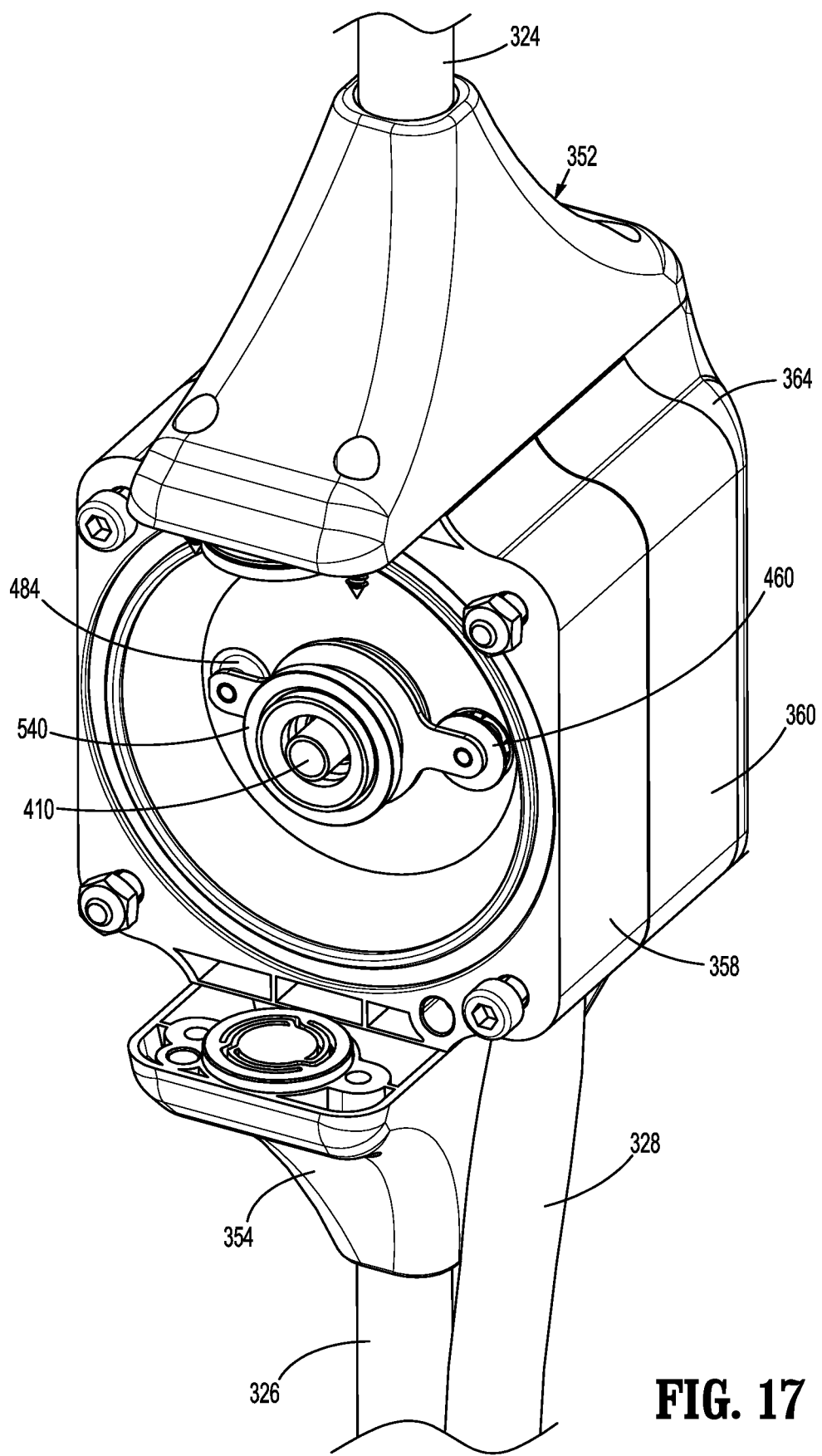
FIG. 17 is a side perspective view of the fluid pump shown in FIG. 15 with a first pump chamber cover removed.
Figure 19:
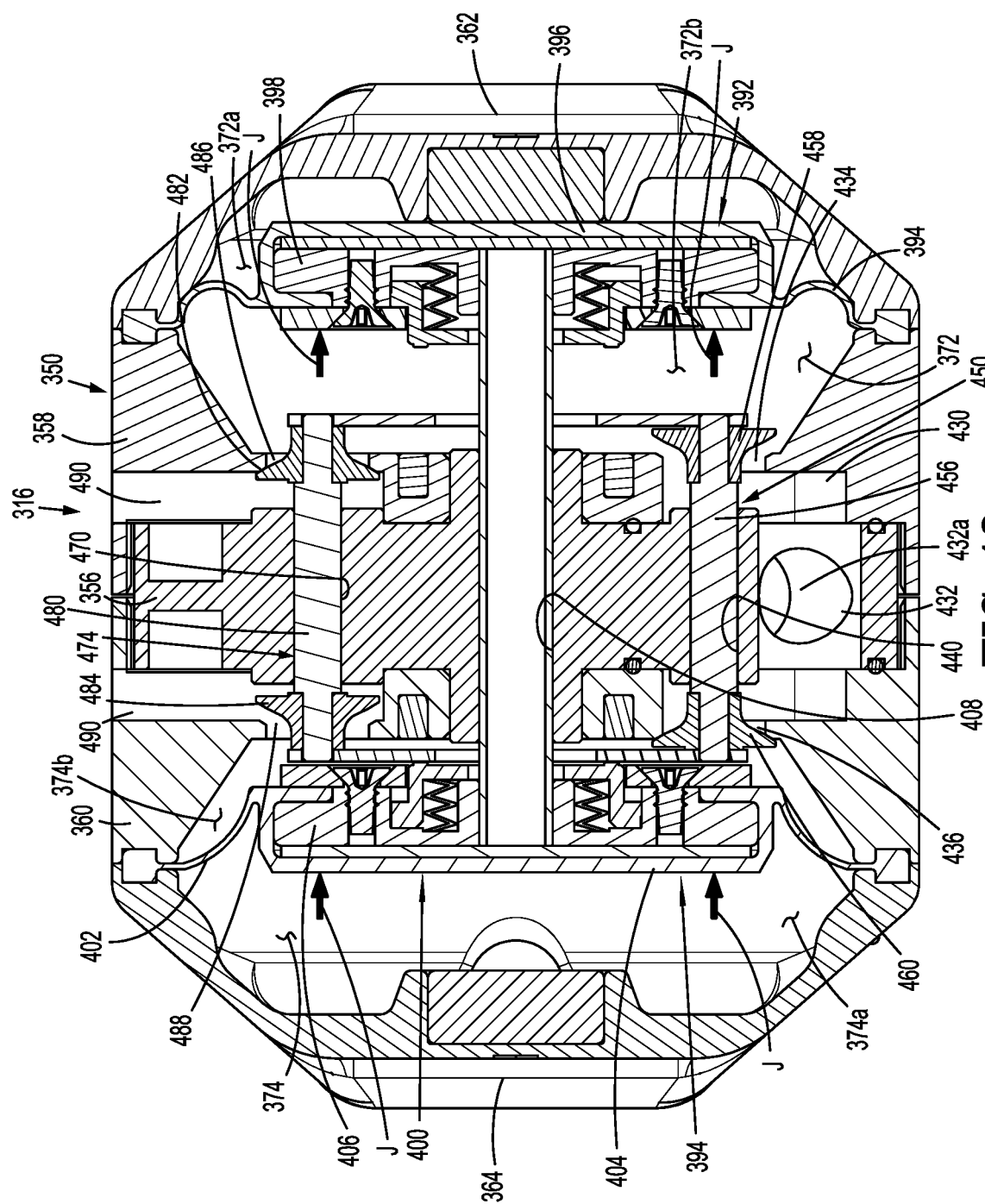
FIG. 19 is a cross-sectional view taken along section line 19-19 of FIG. 18.

FIG. 19 illustrates a cross-sectional view of the fluid pump 316 showing a vacuum chamber 430 defined within the housing 350. The central housing portion 356 and the first and second body portions 358, 360 of the housing 350 of the fluid pump 316 define the vacuum chamber 430 and a vacuum port 432. The vacuum port 432 is coupled to a vacuum source 14 (FIG. 1) by a conduit 328 (FIG. 14). As illustrated in FIG. 14, in use, the conduit 328 is oriented vertically and extends from a lower end of the housing 316.

The vacuum port 432 defines a channel 432a that communicates with the vacuum chamber 430. The first body portion 358 defines a bore 434 that communicates the vacuum chamber 430 with the vacuum cavity 372b of the first pump chamber 372. Similarly, the second body portion 360 defines a bore 436 that communicates the vacuum chamber 430 with the vacuum cavity 374b of the second pump chamber 374. The bores 434, 436 are provided to apply a vacuum to the vacuum cavities 372b, 374b of the first and second pump chambers 372, 374 of the fluid pump 16 to control movement of the diaphragms 394, 400 within the first and second pump chambers 372, 374, respectively, as described in more detail below.

The central housing portion 356 of the housing 350 of the fluid pump 316 defines a bore 440 that receives a vacuum valve assembly 450. The vacuum valve assembly 450 includes a valve shaft 456 and valve members 458, 460 that are positioned to alternately seal the bores 434, 436 of the first and second body portions 358, 360, respectively. The valve shaft 356 connects the valve member 458 to the valve member 460 and is movable between a first end stroke position in which the valve member 458 fully seals the bore 434 of the first body portion 358 while the bore 436 of the second body portion 360 remains unsealed and a second end stroke position in which the valve member 460 fully seals the bore 436 of the second body portion 360 while the bore 434 of the first body portion 358 remains unsealed. As used herein, "end stroke position" means the position in which the valve shaft is at one of the ends of it stroke with one valve fully open and the other valve fully closed.

The central housing portion 356 of the housing 350 of the fluid pump 316 also defines a bore 470 (FIG. 19) that receives an atmosphere valve assembly 474. The first and second body portions 358, 360 define bores 486, 488, respectively. The atmosphere valve assembly 474 includes a valve shaft 480 and valve members 482, 484 that are positioned to alternately seal the bores 486, 488 as the valve shaft 480 moves between its end stroke positions. The bores 486, 488 connect the vacuum cavities 372b, 374b of the first and second pump chambers 372, 374 with atmosphere channels 490 formed in the first and second body portions 358, 360. The valve shaft 480 connects the valve member 482 to the valve member 484 and is movable within the bore 470 between a first end stroke position in which the valve member 482 seals the bore 486 of the first body portion 358 while the bore 488 of the second body portion 360 remains unsealed (FIG. 21) and an end stroke second position in which the valve member 484 seals the bore 488 of the second body portion 360 while the bore 486 of the first body portion 358 remains unsealed (FIG. 19).

Referring to FIGS. 18 and 19, when the diaphragm 400 moves in the direction indicated by arrows "J" to a position to collapse the vacuum cavity 374b of the second pump chamber 374, the end of the valve shaft 480 of the atmosphere valve assembly 474 and the end of the valve shaft 456 of the vacuum valve assembly 450 that are positioned within the second pump chamber 374 are engaged by the shaft holder 406. As the shaft holder 406 moves in the direction of arrows "J", the valve member 484 of the atmosphere valve assembly 474 moves to a position to unseal the bore 488 connecting the vacuum cavity 374b of the second pump chamber 374 to the atmosphere channels 490 and the valve member 482 moves to a position to seal the bore 486 connecting the vacuum cavity 372b of the first pump chamber 372 to the atmosphere channels 490. Similarly, as the shaft holder 406 moves in the direction of arrows "J", the valve shaft 456 of the vacuum valve assembly 450 moves the valve member 460 of the vacuum valve assembly 450 to a position to seal the bore 436 connecting the vacuum chamber 430 to the vacuum cavity 374b and the valve member 458 moves to a position to unseal the bore 434 connecting the vacuum chamber 430 to the vacuum cavity 372b of the first pump chamber 372. As the diaphragm 400 in the second pump chamber 374 moves to the position in which the vacuum chamber 374b is collapsed, the fluid cavity 374a of the pump chamber 374 is expanded to draw fluid into the fluid cavity 372a through the check valve 388 (FIG. 18). As the diaphragm 394 in the second pump chamber 374 moves in the direction indicated by arrows "J", irrigation fluid is forced from the fluid cavity 372a of the first pump chamber 372 through the check valve 382 and into the fluid outlet manifold 354.

Figure 21:
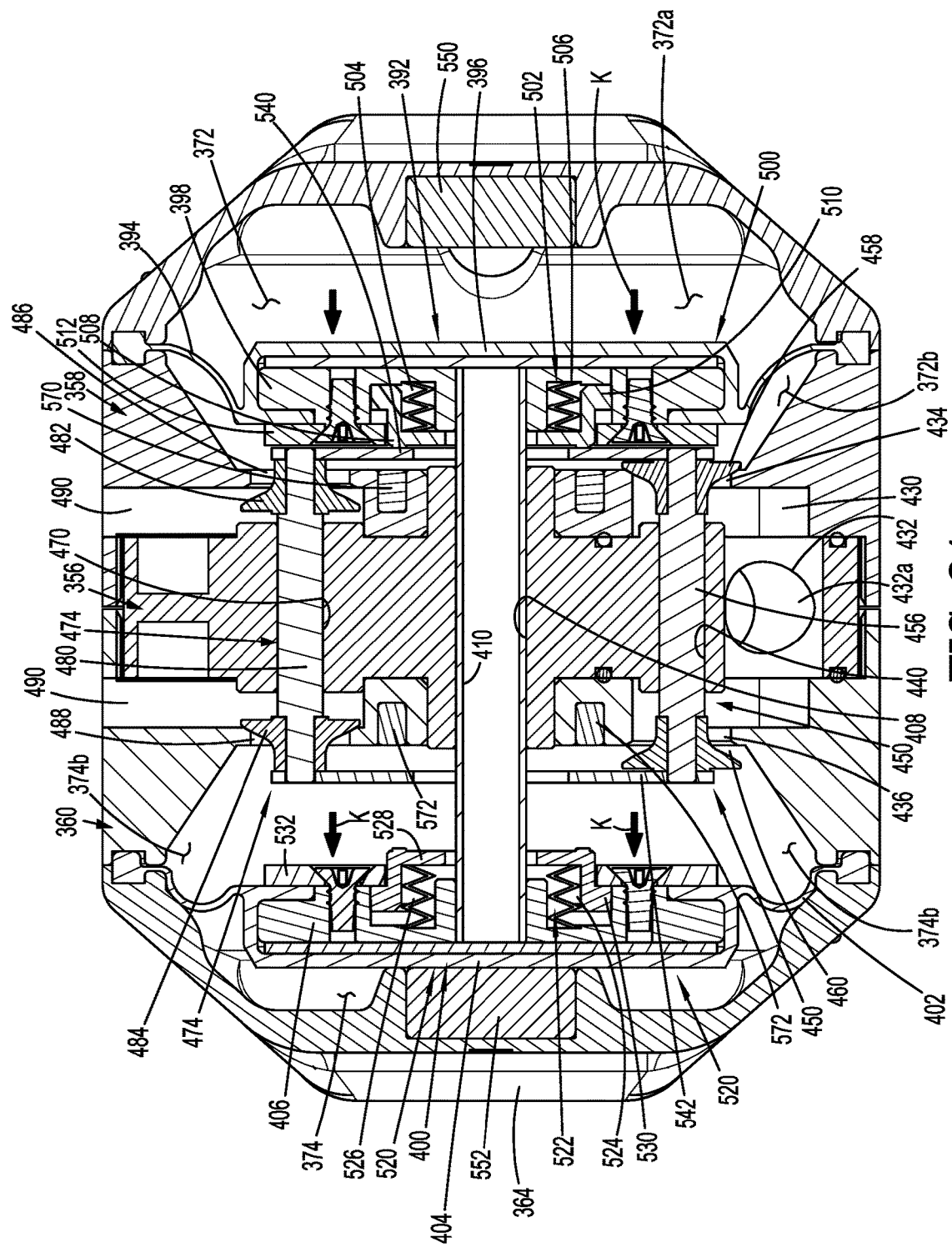
FIG. 21 is a cross-sectional view taken along section line 21-21 of FIG. 20.

When the valve shaft 456 of the vacuum valve assembly 450 moves to the position shown in FIG. 19 such that the bore 434 is unsealed and the bore 436 is sealed, the vacuum cavity 372b of the first pump chamber communicates with the vacuum chamber 430 to draw a vacuum in the vacuum cavity 372b of the first pump chamber 372 and the vacuum cavity 374b of the second pump chamber 374 is vented. As illustrated in FIGS. 20 and 21, this difference in pressure in the vacuum cavities 372b, 374b of the first and second pump chambers 372, 374, respectively, causes the diaphragm 392 in the first pump chamber 372 to move in the direction of arrows "K" to collapse the vacuum cavity 372b of the first pump chamber 374. As the vacuum cavity 372b collapses, the fluid cavity 372a of the first pump chamber 372 expands to draw irrigation fluid into the fluid cavity 372a through the first check valve 380 (FIG. 20). As the diaphragm 394 moves in the direction indicated by arrows "K", the piston shaft 410 causes corresponding movement of the diaphragm 400 in the second pump chamber 374 to force irrigation fluid from the fluid cavity 374a of the second pump chamber 374 through the check valve 390 (FIG. 20) and into the outlet manifold 354. As the diaphragm 400 moves in the direction of arrows "K", the vacuum cavity 374b of the second pump chamber 374 is vented through the bore 486 (FIG. 21) via the open valve 482.

As discussed above in regard to shaft holder 406, the shaft holder 398 is positioned to engage the end of the valve shaft 480 of the atmosphere valve assembly 474 and the end of the valve shaft 456 of the vacuum valve assembly 450 when the shaft holder 398 approaches its end stroke position within the first pump chamber 372 This will unseal the bore 436 to connect the vacuum chamber 374b of the second pump chamber 374 to the vacuum chamber 430 and to seal the bore 486 to connect the vacuum cavity 372b of the first pump chamber 372 to the atmosphere channels 490. Once again, this difference in pressure in the vacuum cavities 372b, 374b of the first and second pump chambers 372, 374 causes the diaphragm 394 to change direction to movement in the direction of arrow "J" (FIG. 19) to restart the pump cycle. The diaphragms 394 and 400 will continue to operate in this manner to provide a pressurized supply of irrigation fluid to the irrigation and suction wand 22 (FIG. 1).

The diaphragm 392 forms a piston assembly 500 with the shaft holder 398. In certain aspects of the disclosure, the piston assembly 500 also includes a biasing mechanism 502 that is secured to the side of the shaft holder 398 opposite to the diaphragm 392. In some aspects of the disclosure, the side of the shaft holder 398 opposite to the diaphragm 392 defines an annular recess 504 that receives the biasing mechanism 502 which includes an annular spring 506 and an annular plate 508. The annular plate 508 includes an annular shoulder 510 that is engaged by a locking plate 512 to secure the biasing mechanism 502 within the annular recess 504 for movement between retracted and advanced positions. The annular spring 506 is received within the annular recess 504 and urges the annular spring plate 508 inwardly towards the first body portion 358 of the housing 350. The locking plate 512 can be secured to the shaft holder 398 with screws or the like and is positioned to engage the shoulder 510 of the spring plate 508 to retain the spring plate 508 within the annular recess 504. The annular spring 506 can be in the form of one or more wave springs although the use of other spring types is envisioned.

The diaphragm 400 forms a piston assembly 520 with the shaft holder 406. The piston assembly 520 also includes a biasing mechanism 522 that is secured to a side of the shaft holder 406 opposite to the diaphragm 400. The side of the shaft holder 406 opposite to the diaphragm 400 defines an annular recess 524 that receives the biasing mechanism 522 which includes an annular spring 526 and an annular spring plate 528. The annular spring plate 528 includes an annular shoulder 530 that is engaged by a locking plate 532 to secure the biasing mechanism 522 within the annular recess 524 for movement between retracted and advanced positions. The annular spring 526 is received within the annular recess 524 and urges the annular spring plate 528 towards its advanced position inwardly towards the second body portion 360 of the housing 350. The locking plate 532 can be secured to the shaft holder 406 by screws or the like and is positioned to engage the shoulder 530 of the spring plate 528 to retain the spring plate 528 within the annular recess 524. As with annular spring 506, the annular spring 526 can be in the form of one or more wave springs although the use of other spring types is envisioned. The purpose and operation of the biasing mechanisms 502 and 522 is described in further detail below.

As illustrated in FIG. 21, opposite ends of the valve shaft 456 of the vacuum valve assembly 450 and valve shaft 480 of the atmosphere valve assembly 474 positioned within the first and second pump chambers 372, 374 are secured together by frame members 540 and 542, respectively. The frame members 540 and 542 are formed of a ferromagnetic material and function to couple the valve shafts 456 and 480 together to restrict the vacuum valve assembly 450 and atmosphere valve assembly 474 to unified movement.

The first and second covers 362 and 364 each support an outer magnet 550 and 552, respectively that is positioned to attract one of the piston assemblies 500 and 520 to its end stroke position. The piston assembly 500 includes a piston plate 560 that is formed of a ferromagnetic material and the piston assembly 520 includes a piston plate 562 that is formed of a ferromagnetic material. The magnets 550 and 552 are positioned to ensure that the piston assemblies 500 and 520 are in their end stroke positions when the fluid pump 316 is stopped. When the piston assemblies 500 and 520 are in their end stroke positions, the valve assemblies 450 and 474 are also urged to and retained in their end stroke positions with the valves 456, 458, 482 and 484 in fully open or fully closed positions.

Each of the first and second housing portions 358, 360 also supports an inner magnet 570 and 572, respectively (FIG. 21). In certain aspects of the disclosure, the inner magnets 570 and 572 are annular and are positioned to attract the frame members 540 and 542 to delay opening and closing of the respective valve assemblies 450 and 474 during operation of the fluid pump 316. More specifically, the inner magnets 570 and 572 retain the valve shafts 456 and 480 in their end stroke positions as the piston shaft 410 changes direction to maintain the valves 456, 458, 482 and 484 in their fully open or fully closed positions for a longer period of time to minimize the likelihood of stalling of the fluid pump 316.

The biasing mechanisms 502, 522 also delay the opening and closing of the valves 456, 458, 482 and 484. More specifically, the biasing mechanisms 502, 522 are positioned to engage the respective frame members 540, 542 to urge the frame members 540, 542 and the respective valve assemblies 450 and 474 that the frame members 540, and 542 are coupled to their end stroke positions when the piston assemblies 500 and 520 are positioned adjacent to the first and second body portions 358 and 360 of the housing 350. When the piston shaft 410 of the fluid pump 316 is in an end stroke position, one of the annular plates 508 and 528 of the biasing mechanisms 502, 522 engages a respective frame member 540, 542 to maintain the respective frame member 540, 542 and the respective valve assemblies 450 and 474 in their end stroke positions as the piston shaft 410 changes direction. This engagement, which is maintained as the springs 506 and 526 of the biasing mechanisms 502, 522 expand, delays opening and closing of the respective valve assemblies 450 and 474 as the piston shaft 410 and piston assemblies 500, 520 change direction within the body 350 of the fluid pump 316 during operation of the fluid pump 316. More particularly, when the piston assembly 500 moves towards the first body portion 358 of the housing 350, the plate 508 of the biasing mechanism 502 engages the frame member 540 and pushes the frame member 540 towards the first body portion 358 to move the valve assemblies 450 and 474 to their end stroke position. When the piston assemblies 500, 520 reverse their motion, the inner magnet 570 and the biasing mechanism 502, 522 will retain the frame 540 in position against the first body portion 358 of the housing 350 while the piston assemblies 500, 520 begin to change direction to maintain the valve assemblies 450 and 474 in their current end stroke position. The magnets 550, 552, 570, and 572 ensure that the piston assemblies 500, 520 are not in transit, i.e., between fully open and fully closed positions, when the fluid pump 316 is stopped to facilitate restart of the fluid pump 316. The biasing mechanisms 502 and 522 are configured to delay transitioning of the valve assemblies 450 and 474 by about 1 mm of stroke of the piston shaft 410 to reduce transition losses.

The biasing mechanisms 502 and 522, the frame members 540 and 542, and the magnets 550, 552, 570, and 572 minimize the portion of the stroke of the piston shaft 410 in which the valve assemblies 150 and 174 are in a transit state, i.e., when all of the valves controlling a vacuum state within the vacuum cavities 372b and 374b of the first and second pump chambers 372 and 374, respectively, are open or between their end stroke positions. The transit state depletes the vacuum from both of the vacuum cavities 372b and 374b. In this position, the pump 316 would never restart. The mechanisms described above prevent stoppage of the fluid pump in the transit state.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspects of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A vacuum assisted suction and irrigation system comprising:
   a suction and irrigation wand including a proximal body portion supporting a suction valve and an irrigation valve and a distal body portion defining a fluid channel;
   an irrigation fluid supply connected to the irrigation valve of the suction and irrigation wand, the irrigation valve being actuable to deliver irrigation fluid to the fluid channel of the suction and irrigation wand;
   a vacuum source connected to the suction valve of the suction and irrigation wand, the suction valve being actuable to draw a vacuum within the fluid channel;
   a fluid pump configured to deliver irrigation fluid to the suction and irrigation wand, the vacuum source connected to the fluid pump to pressurize the irrigation fluid being delivered to the suction and irrigation wand, the fluid pump including a first pump chamber and a second pump chamber, the first pump chamber being divided into a first vacuum cavity and a first fluid cavity by a first diaphragm and the second pump chamber being divided into second vacuum cavity and a second fluid cavity by a second diaphragm, the first diaphragm supporting a first piston and the second diaphragm supporting a second piston, the first piston coupled to the second piston by a piston shaft, the fluid pump including a vacuum chamber and an atmosphere channel, the vacuum chamber communicating with the vacuum source and the atmosphere channel communicating with atmosphere; and
   a vacuum valve assembly movable from a first position in which the first vacuum cavity communicates with the vacuum chamber and the second vacuum cavity is sealed from the vacuum chamber and a second position in which the second vacuum cavity communicates with the vacuum chamber and the first vacuum cavity is sealed from the vacuum chamber, wherein the first and second pistons are movable into engagement with the vacuum valve assembly to move the vacuum valve assembly between the first and second positions.

2. The suction and irrigation system of claim 1, wherein the fluid pump includes an atmosphere valve assembly, a first bore communicating the first vacuum cavity with the atmosphere channel, and a second bore communicating the second vacuum cavity with the atmosphere channel.

3. The suction and irrigation system of claim 2, wherein the atmosphere valve assembly includes a first valve member and a second valve member, the atmosphere valve assembly being movable between a first position in which the first valve member seals the first bore and the second bore is unsealed, and a second position in which the second seal member seals the second bore and the first bore is unsealed.

4. The suction and irrigation system of claim 3, wherein the fluid pump includes a third bore communicating the first vacuum cavity with the vacuum chamber, and a fourth bore communicating the second vacuum cavity with the vacuum chamber.

5. The suction and irrigation system of claim 4, wherein the vacuum valve assembly includes a third valve member and a fourth valve member, the vacuum valve assembly being movable between the first position in which the third valve member seals the third bore and the fourth bore is unsealed, and the second position in which the fourth seal member seals the fourth bore and the third bore is unsealed.

6. The suction and irrigation system of claim 5, wherein the first valve member is coupled to the second valve member by a first valve shaft and the third valve member is coupled to the fourth valve member by a second valve shaft.

7. The suction and irrigation system of claim 6, further including a first frame member and a second frame member, the first frame member interconnecting first ends of the first and second valve shafts and the second frame member interconnecting second ends of the first and second valve shafts.

8. The suction and irrigation system of claim 7, further including an inner magnet supported on the body adjacent each of the first and second vacuum cavities of the first and second pump chambers, each of the inner magnets being positioned to attract a respective one of the first and second frame members to urge the atmosphere valve assembly and the vacuum valve assembly towards one of their end stroke positions.

9. The suction and irrigation system of claim 8, wherein each of the first and second pistons supports a biasing mechanism, the biasing mechanism positioned to engage a respective one of the first and second frame members to urge the first and second valve shafts to their end stroke positions and delay transitioning of the atmosphere valve assembly and the vacuum valve assembly from one of their first and second end stroke positions to the other of their end stroke positions.

10. The suction and irrigation system of claim 9, wherein the first and second biasing mechanisms each include an annular spring and an annular plate, the annular spring being compressible and expandable to maintain the annular plate in engagement with a respective one of the frame members to maintain the atmosphere valve assembly and the vacuum valve assembly in its end stroke position as the piston shaft changes direction.

11. The suction and irrigation system of claim 8, further including an outer magnet supported on the body adjacent each of the first and second fluid cavities of the first and second pump chambers, the outer magnets being positioned to draw a respective one of the first and second pistons towards one of its end stroke positions when the fluid pump is stopped to facilitate restart of the fluid pump.

12. The suction and irrigation system of claim 1, wherein the irrigation fluid supply includes a compressible pouch containing an irrigation fluid.

13. The suction and irrigation system of claim 7, wherein the fluid pump includes a base member and a compression member, the compression member having a first end pivotally coupled to the base member.

14. The suction and irrigation system of claim 8, wherein the compressible pouch is positioned between the base member and the compression member.

15. The suction and irrigation system of claim 9, wherein the fluid pump includes a bellows that is attached to the base member and the compression member, the bellows being movable between a contracted position and an expanded position to control the pressure of irrigation fluid within the compressible pouch.

16. A fluid pump comprising:
a body defining a first pump chamber, a second pump chamber, a vacuum chamber, and an atmosphere channel, the vacuum chamber communicating with the vacuum source and the atmosphere channel communicating with atmosphere;
a first diaphragm dividing the first pump chamber into a first vacuum cavity and a first fluid cavity;
a second diaphragm dividing the second pump chamber into second vacuum cavity and a second fluid cavity;
a first piston supported by the first diaphragm;
a second piston supported by the second diaphragm, wherein the first piston is coupled to the second piston by a piston shaft, the first and second pistons being movable in unison between first and second end stroke positions;
a first bore communicating the first vacuum cavity with the atmosphere channel, a second bore communicating the second vacuum cavity with the atmosphere channel, a third bore communicating the first vacuum cavity with the vacuum chamber, and a fourth bore communicating the second vacuum cavity with the vacuum chamber;
an atmosphere valve assembly including a first valve member and a second valve member, the atmosphere valve assembly being movable between a first end stroke position in which the first valve member seals the first bore and the second bore is unsealed, and a second end stroke position in which the second seal member seals the second bore and the first bore is unsealed, the first valve member coupled to the second valve member by a second piston shaft;
a vacuum valve assembly including a third valve member and a fourth valve member, the vacuum valve assembly being movable between a first end stroke position in which the third valve member seals the third bore and the fourth bore is unsealed, and a second end stroke position in which the fourth seal member seals the fourth bore and the third bore is unsealed, the third valve member coupled to the fourth valve member by a third piston shaft; and
first and second frame members, the first frame member interconnecting first ends of the second and third piston shafts and the second frame member interconnecting second ends of the second and third piston shafts.

17. The fluid pump of claim 16, further including an inner magnet supported on the body of the fluid pump adjacent each of the first and second vacuum cavities of the first and second pump chambers, each of the inner magnets being positioned to attract a respective one of the first and second frame members to urge the vacuum valve assembly and the atmosphere valve assembly towards one of their first and second end stroke positions.

18. The fluid pump of claim 17, wherein each of the first and second pistons supports a biasing mechanism, the biasing mechanism positioned to engage a respective one of the first and second frame members to urge the first and second piston shafts towards their end stroke positions to delay transitioning of the atmosphere valve assembly and the vacuum valve assembly from one of their first and second end stroke positions towards the other of the first and second end stroke positions.

19. The fluid pump of claim 18, wherein the first and second biasing mechanisms each include an annular spring and an annular plate, the annular spring being compressible and expandable to maintain the annular plate in engagement with a respective one of the frame members to maintain the atmosphere valve assembly and the vacuum valve assembly in one of its first and second end stroke position as the first piston shaft changes direction.

20. The fluid pump of claim 16, further including an outer magnet supported on the body adjacent each of the first and second fluid cavities of the first and second pump chambers, the outer magnets being positioned to draw a respective one of the first and second pistons towards its end stroke position when the fluid pump is stopped to facilitate restart of the fluid pump.

21. A fluid pump comprising:
a body defining a first pump chamber, a second pump chamber, a vacuum chamber, and an atmosphere channel, the vacuum chamber communicating with the vacuum source and the atmosphere channel communicating with atmosphere;
a first diaphragm dividing the first pump chamber into a first vacuum cavity and a first fluid cavity;
a second diaphragm dividing the second pump chamber into second vacuum cavity and a second fluid cavity;
a first piston supported by the first diaphragm;
a second piston supported by the second diaphragm, wherein the first piston is coupled to the second piston by a first piston shaft, the first and second pistons being movable in unison between first and second end stroke positions;
a first bore communicating the first vacuum cavity with the atmosphere channel, a second bore communicating the second vacuum cavity with the atmosphere channel, a third bore communicating the first vacuum cavity with the vacuum chamber, and a fourth bore communicating the second vacuum cavity with the vacuum chamber;
a atmosphere valve assembly including a first valve member and a second valve member, the atmosphere valve assembly being movable between a first end stroke position in which the first valve member seals the first bore and the second bore is unsealed, and a second end stroke position in which the second seal member seals the second bore and the first bore is unsealed, the first valve member coupled to the second valve member by a second piston shaft;
a vacuum valve assembly including a third valve member and a fourth valve member, the vacuum valve assembly being movable between a first end stroke position in which the third valve member seals the third bore and the fourth bore is unsealed, and a second end stroke position in which the fourth seal member seals the fourth bore and the third bore is unsealed, the third valve member coupled to the fourth valve member by a third piston shaft; and
an outer magnet supported on the body adjacent each of the first and second fluid cavities of the first and second pump chambers, the outer magnets being positioned to draw a respective one of the first and second pistons towards its end stroke position when the fluid pump is stopped to facilitate restart of the fluid pump.

* * * * *